(12) United States Patent
von Blumenthal

(10) Patent No.: US 8,718,954 B2
(45) Date of Patent: May 6, 2014

(54) PROCESS FOR OPERATING A GAS SAMPLING DEVICE FOR COLORIMETRIC GAS ANALYSIS

(75) Inventor: Tilman von Blumenthal, Lübeck (DE)

(73) Assignee: Dräger Safety AG & Co. KGaA, Lübeck (DE)

( * ) Notice: Subject to any disclaimer, the term of this patent is extended or adjusted under 35 U.S.C. 154(b) by 409 days.

(21) Appl. No.: 13/169,324

(22) Filed: Jun. 27, 2011

(65) Prior Publication Data

US 2012/0052590 A1 Mar. 1, 2012

(30) Foreign Application Priority Data

Aug. 28, 2010 (DE) .......................... 10 2010 035 728

(51) Int. Cl.
*G01N 21/75* (2006.01)

(52) U.S. Cl.
USPC .......................................................... 702/47

(58) Field of Classification Search
USPC .......................................................... 702/47
See application file for complete search history.

(56) References Cited

U.S. PATENT DOCUMENTS

| | | | |
|---|---|---|---|
| 5,207,089 A | * | 5/1993 | Abt et al. ........................... 73/37 |
| 5,295,790 A | | 3/1994 | Bossart et al. |
| 6,112,576 A | * | 9/2000 | Tsopelas et al. .............. 73/25.02 |

FOREIGN PATENT DOCUMENTS

| | | |
|---|---|---|
| DE | 3937641 A1 | 1/1991 |
| DE | 693 10 560 T2 | 11/1997 |
| DE | 198 25 103 A1 | 12/1998 |
| DE | 101 31 688 B4 | 5/2006 |
| EP | 0392486 A1 | 10/1990 |

OTHER PUBLICATIONS

William J. Alvesteffer, Laminar Flow Element With a Linear Pressure Drop Versus Volumetric Flow, Teledyne Hastings Instruments, 1998 ASME Fluids Engineering Division Summer Meeting, Jun. 21-25, 1998, Washington, DC, 5 pages.*

* cited by examiner

*Primary Examiner* — Tung S Lau
(74) *Attorney, Agent, or Firm* — McGlew and Tuttle, P.C.

(57) ABSTRACT

A process for controlling the delivery of a quantity of gas to be measured through a test gas tube (60) with a pump (20), a sensor system for pressure and flow measurement (12, 14, 16) and a control and regulating unit (30). A common mode offset of a differential pressure sensor (14), determined in a calibration process, is taken into account in the process for operating the gas sampling device to increase the accuracy of a gas volume being delivered with pump (20) from the measuring environment (50).

20 Claims, 9 Drawing Sheets

US 8,718,954 B2

PROCESS FOR OPERATING A GAS SAMPLING DEVICE FOR COLORIMETRIC GAS ANALYSIS

CROSS REFERENCE TO RELATED APPLICATIONS

This application claims the benefit of priority under 35 U.S.C. §119 of German Patent Application DE 10 2010 035 728.6 filed Aug. 28, 2010, the entire contents of which are incorporated herein by reference.

FIELD OF THE INVENTION

The present invention pertains to a process for controlling and regulating a device for sampling gas with a pump for delivering a quantity of gas to be measured through a test gas tube, with a sensor system for pressure and flow measurement and with a control and regulating unit for controlling and regulating the calibration and checking the measuring operation. The present invention pertains, furthermore, to a means for controlling and regulating the quantity of gas to be measured and to a means for controlling and regulating the pressure level needed for transporting the quantity of gas to be measured.

BACKGROUND OF THE INVENTION

Gas detectors and measuring devices are used to detect or measure percentages of foreign gases in the composition of industrial gases in gas tanks or gas line systems, e.g., compressed air lines.

Another field of application for gas detectors and gas measuring devices is to detect trace gases in ambient air. The quantity of gas to be analyzed is sent in a group of these gas detectors through a test tube, in which a detection reagent for the particular component to be determined is contained, the detection reaction taking place as a chromatic reaction while a change in color takes place.

A certain quantity of gas is drawn through the test tube by means of a pump driven manually or by a motor.

Such test tubes are used, for example, in the working environment of civil protection or in the maintenance of industrial plants to rule out endangerment to the rescue or maintenance teams by explosive or toxic gas components.

Bellows, diaphragm or reciprocating pumps as well as double piston diaphragm pumps are used as pumps here.

A combination of test gas tube and a controlled pump for application of a volume through a test tube is described in U.S. Pat. No. 5,295,790 A.

The combination of pressure sensors with a laminar flow element for flow measurement in a gas sampling device for determining the properties of the gas, which combination is known from U.S. Pat. No. 5,295,790 A, makes possible a linear detection of the volume flow as a function of the differential pressure dropping over the laminar flow element in the laminar range of flow in the laminar flow element. The pressure dropping over the laminar flow element is converted into an electric output signal by means of a differential pressure sensor.

This combination of a laminar flow element and a pressure sensor is a common method according to the state of the art for obtaining a linear output signal proportional to the flow. The span of the measuring range that can be obtained with such a combination of a differential pressure sensor and laminar flow element is typically in the range of 1:10 to 1:20 between the lowest measurement value that can be detected within the required measuring accuracy and the maximum detectable measured value. If the span of the measuring range shall be expanded, one typically switches over to a second measuring range with another differential pressure sensor by means of a valve. The lowest measured value and its measuring accuracy are determined by the resolution capacity and the reproducibility of the pressure sensor system and by the error effects of the gas sampling device and pressure sensor system used. The maximum detectable value is determined by both the maximum allowable pressure drop in the measuring range of the device for a reliable measurement and by the fact that laminarization by the laminar flow element is no longer effective above a certain flow rate. The consequence of a no longer effective laminarization is that the linear relationship between pressure drop and flow rate is no longer given.

An essential element concerning the measuring accuracy at the lower limit of the measuring range is the systematic measuring accuracy of the pressure sensor. Pressure sensors are subject at the attainable accuracies to the influencing variables of the environment, especially the ambient temperature and ambient pressure. Especially in a pressure sensor that detects the pressure as a measured variable by means of a deflection of a measuring diaphragm, the measurement result is affected by the ambient pressure by causing a prestress of the diaphragm, on the one hand, and, on the other hand, by the ambient temperature due to thermal expansion of the diaphragm.

DE 10131688 B4 describes a pressure sensor, in which the effect of ambient temperature is compensated by selecting a suitable combination of materials for the measuring diaphragm. The effect of ambient pressure on the measurement result cannot be compensated by means of a suitable combination of materials as a design feature.

DE 2823315 describes a control of a tube pump with a constant pressure drop over the test tube as a controlled variable.

DE 19 825103 A1 describes a volume control of a test tube pump, wherein a differential pressure sensor is used in combination with a flow resistance for controlling the volume.

A laminar flow element (LFE) represents a flow resistance in such an application, with the peculiarity that the flow is laminarized in a defined flow range.

The effect of ambient pressure on the determination of the volume being delivered through the test tube is not taken into account in DE 19 825103 A1.

It is necessary for the universal applicability of the tube pump for various types of gas detector tubes that the quantity delivered by the tube pump be adaptable to the different types of gas detector tubes. It is advantageous for this that the tube pump draw the quantity of gas to be measured through the test tube under a constant vacuum of, for example, 100 mbar, as it is described in U.S. Pat. No. 5,295,790 A.

Depending on the type of tube and flow resistance thereof, a flow rate of 50-60 mL/min to 2-3 L/min is established. The flow rate detected by means of the differential pressure sensor in combination with a laminar flow element is integrated into a gas volume and compared with the desired volume specific of the type of tube. The pump is switched off when the desired volume is reached.

It is absolutely necessary for a subsequent colorimetric analysis and the measuring accuracy that can be achieved overall that the desired volume of the quantity of gas drawn through the test gas tube from the measuring environment is maintained highly accurately. The difficulty in obtaining a flow rate accurately, reproducibly and with a constant relative accuracy in the range of <5% over a broad span of measuring range with a single combination of differential pressure sensor and laminar flow element to guarantee the requirements imposed on maintaining the desired volumes specific of the different types of tubes arises in conjunction with the broad span of measuring range required by the great variety of tube types. It is necessary for this that the effect of ambient pressure on the measuring accuracy of the differential pressure sensor be likewise compensated besides the compensation of the effect of ambient temperature on the measuring accuracy of the differential pressure sensor.

SUMMARY OF THE INVENTION

The object of the present invention is therefore to propose a process for operating a gas sampling device for colorimetric gas analysis, so that the admitted gas volume delivered through the test gas tube is maintained accurately.

According to the invention, a process is provided for operating a gas sampling device for colorimetric gas analysis. The process comprises the steps of providing a control and regulating unit, an energy supply unit, a memory, a laminar flow element, a pressure sensor, a differential pressure sensor and a pump and performing a volume measurement and a flow measurement in one measuring operation by means of the laminar flow element and the differential pressure sensor. At least one initial correction parameter and/or at least one current correction parameter is used as the correction parameter for the conversion of the differential pressure value into a volume value.

A gas sampling device for colorimetric gas analysis comprises according to the present invention a delivery means for delivering a predetermined and defined volume of ambient air through a test gas tube. After a predetermined volume typical of a certain type of test gas tube has flown through, a component of a toxic gas being sought, which is present in the ambient air, can be detected from a color change visible on the test gas tube. A regulated pump, which draws ambient air through the test gas tube by a vacuum, is preferably used as a delivery means. The pressure level of the pump is regulated, the quantity of air delivered through the test gas tube is monitored by means of a flow measuring means and summation to a volume, and the delivery of air through the test gas tube is terminated by switching off the pump when a predetermined target volume is reached. The flow measuring means used to monitor the volume comprises a flow resistance designed as a laminar flow element and a differential pressure sensor, said differential pressure sensor detecting a decreasing pressure drop proportional to the flow flowing through. The pressure drop is converted by means of a systematic pressure-vs.-flow characteristic of the laminar flow element into a flow value. This arrangement comprising laminar flow element and differential pressure sensor is especially advantageous because, on the one hand, no energy is introduced into the gas, which could consist of an ignitable gas mixture under certain circumstances, where any introduction of energy is to be avoided under any circumstances, for example, in a hot wire sensor, and, on the other hand, no moving parts are necessary, which would make the arrangement sensitive to shocks, as it happens, for example, in a rotary flow meter. To obtain a simple and robust arrangement, the process according to the present invention uses only a single differential pressure sensor for detecting the differential pressure dropping over the laminar flow element. Since a measuring span of nearly 1:40 is necessary for the span of the measuring range because of the possibility of using different test gas tubes from 0.05 L/min to 2 L/min, a plurality of differential pressure sensors and additional switching means, for example, valves, would be necessary. Such additional switching have a certain fault susceptibility due to shocks and function reliably and accurately for a limited number of switching operations only. This is in conflict with the principle of a simple and robust arrangement. It is therefore proposed according to the present invention that the measuring span of an arrangement comprising a differential pressure sensor and a laminar flow element be expanded by calibrating the differential pressure sensor in a calibration operation and by using the calibration values obtained during the calibration during the operation of the gas sampling device.

A gas sampling device according to the present invention comprises an arrangement with a connection element for connection with a test gas tube, a filter element for retaining contaminants, a flow resistance designed as a laminar flow element, a buffer volume, a first pressure sensor for detecting the vacuum present at the test gas tube in relation to the environment, a second pressure sensor for detecting the pressure drop over the flow resistance, a pump for generating the vacuum and for drawing air from the measuring environment into the test gas tube and a gas outlet element for removing the quantity of gas delivered by the pump into the environment. Furthermore, a memory for storing calibration and status data is provided. As another element, a control and regulating unit, which detects and processes the signals of pressure sensors, writes data in memory areas of the memory and/or reads data therefrom, as well as determines a set point for actuating the pump in a control circuit by comparing desired values and actual values, converts same into an electric manipulated variable and actuates the pump, is arranged in the device. The processing of signals in the control and regulating unit comprises in the sense of the present invention signal amplification elements, analog and/or digital signal filtering elements, analog-to-digital conversion elements and methods for signal improvement, such as mean value formation, noise and interference signal suppression. The control circuit for regulating a pressure level in the gas sampling device comprises in the sense of the present invention both regulating elements implemented according to analog technology and digital control circuits as well as combinations of analog and digital control circuit elements. The conversion of set points at the output of the control circuit into electric manipulated variables for actuating the pump takes place in the sense of the present invention by a digital-to-analog conversion by means of digital-to-analog conversion elements and/or signal amplification, buffering and driver stages. Furthermore, the signals of the pressure sensors provided according to the present invention in the gas sampling device may be sent both as analog voltage or current signals, for example, in the form of a 0-10 V voltage or 4-20 mA current interface to the control and regulating unit and as a data interface of a digital design, for example, in the form of a fieldbus or industry bus interface with a data communication according to a preset protocol (CAN bus, HART interface, LAN, Ethernet, PROFIBUS, INTERBUS) to the control and regulating unit. The digital design of the interface may be embodied at the signal level by modulation methods (FSK, PSK) in combination with an energy supply of the sensors. The pump is actuated, the pump output is regulated and the pump is also stopped by the control and regulating unit during the operation of the gas sampling device. A quantity of gas to be measured is drawn by the pump through the test gas tube from the measuring environment via the connection element, and the quantity of gas being delivered flows in a serial arrangement at first through the test gas tube, then the filter element, the laminar flow element, then the buffer volume, subsequently the pump and it finally flows off into the environment through the gas outlet element. The first pressure sensor is designed as an absolute pressure sensor and is arranged with a first measuring connection at the inlet of the laminar flow element. The first pressure sensor detects the absolute pressure currently present at the inlet of the laminar flow element. The second pressure sensor is designed as a differential pressure sensor and is arranged with a second measuring connection at the inlet of the laminar flow element and is arranged with a third measuring connection at the outlet of the laminar flow element. The second pressure sensor detects the pressure dropping over the laminar flow element as a differential value. The device comprises, furthermore, a control and regulating unit, which receives the signals of the first and second pressure sensors and assumes actuation of the pump, as well as a memory for storing characteristics and calibration data and an energy supply unit for supplying the gas sampling device with electric energy.

In a special embodiment variant, the gas sampling device is provided with expanded components and functionalities in order to design the operation and course of the measuring operation and calibration in interplay with the user. A data interface is provided for this purpose in order to exchange data, for example, status reports, such as energy supply status, status of the pressure sensors, pump, filter element or laminar flow element, as well as signals of the pressure sensors unidirectionally or bidirectionally with external devices. Such an external device is, for example, a testing means, which is necessary for a final testing or calibration. The external device is connected to the data interface, and the connection may be designed as a direct or indirect connection. A direct connection may be an electric or optical line connection, and an indirect connection may be designed as a telemetric, inductive or infrared optical connection. Additional data transmission elements, such as wired (LAN) or wireless (WLAN) networks may also be incorporated for establishing a connection between the gas sampling device and external device. This makes possible a remote-controlled status detection and status monitoring as well as a remote-controlled calibration of the gas sampling device. Furthermore, a reading unit, for example, a reading device for bar codes or radio frequency identification (RFID) may be connected to the data interface to read in specific data of the test gas tubes. Such a reading unit 13 may be, for example, both part of the gas sampling device and it may also be connected as an external device to the gas sampling device via the data interface. The test gas tubes or the packing of the test gas tubes contains in such a case corresponding identification elements such as bar codes or RFID transponders (RFID tags).

The energy supply of the gas sampling device is designed in a special embodiment as a mobile hand-held device in the form of a battery module, and both primary batteries and rechargeable batteries (storage batteries) are suitable for mobile use. Connection of an external power pack may also be additionally provided for a temporary stationary use as a direct supply of the gas sampling device and/or for charging the rechargeable batteries. The energy supply may be designed in a special manner in the form of an inductive charging and holding device, and the data interface may be arranged combined with the inductive charging and holding device in another manner, so that there is an electric energy supply and data exchange between the gas sampling device and external devices without additional connections being necessary. Both the described variants of the gas sampling device with said components and solutions in which individual components are combined with one another are covered in the sense of the present invention, and it is possible, for example, by the use of a microcontroller (μC) or programmed logic components, to embody data interfaces, data protocol conversion, control and regulating components, signal conversion such as analog/digital conversion or digital/analog conversion and signal processing, such as filtering and mathematical functions in compact modules.

In an alternative embodiment, a third pressure sensor is present, which detects the current barometric air pressure of the environment and sends it to the control and regulating unit.

During the measuring operation, the pump generates a preset vacuum, whose maintenance is monitored by means of the first pressure sensor in conjunction with the control and regulating unit. The changes in the differential pressure present over the laminar flow element are detected by means of the second pressure sensor as a function of time and converted into a flow value by means of the systematic pressure-vs.-flow characteristic of the laminar flow element.

A first correction parameter and a second correction parameter are used during the conversion of the differential pressure value into the flow value. The conversion of the differential pressure measured values into a volume flowing through the test gas tube is carried out by summation over differential pressure measured values for a volume flow according to the determined integral according to Formula 1 below. Volume V is obtained as an integral over a volume flow as a function of time.

The volume [V] is obtained as a function [t] of the differential pressure measured values ΔP and of the first correction parameter [k1] and as a function of the rheological properties of the laminar flow element [LFE] and as a function of the second correction parameter [k2].

$$V = \int_{t1}^{t2} \dot{V}[\Delta P(k1); LFE; k2] dt \quad [1]$$

In equation [1],
V is the volume flow,
$V_{sum}$ is the volume that is delivered through the test gas tube and the laminar flow element by means of the pump,
t1 is the time at which the summation under the determined integral starts,
t2 is the time at which the summation under the determined integral stops,
k1 is the first correction parameter,
k2 is the second correction parameter,
dt is the time as a reference variable of the determined integral, and
LFE represents the rheological properties of the laminar flow element.

The first correction parameter (k1) takes into account a zero point shift of the signal of the second pressure sensor designed as a differential pressure sensor, i.e., that a signal differing from zero is sent by the second pressure sensor even in the case in which the differential pressure at the second pressure sensor represents the real value zero. The second correction parameter (k2) takes into account the rheological properties, e.g., the typical flow resistance of the laminar flow element in combination with certain, preset and known properties of the gas, for example, density, viscosity, moisture content, temperature, and temperature properties of the viscosity. The second correction parameter thus takes into account, besides the properties of the laminar flow element, which are defined rather mechanically in the flow resistance, the particular systematic relationship between flow rate and pressure drop for different industrial gases, as well as flow conditions at the inlet and outlet of the laminar flow element, which likewise affect the differential pressure measurement.

The integral of the flow value is formed continuously over the measurement time elapsed since the start of the measurement and is continuously updated as a volume value, converted into a volume value under standard conditions (1,013 mbar, 20° C.) and compared with a preset desired volume. As soon as the current volume converted for standard conditions exceeds the preset desired volume, the pump is actuated such that no more volume is delivered. Pressure equalization to the current ambient pressure takes place in the device, so that the pressure difference seeks to reach zero in the entire device and also over the laminar flow element, and the first pressure sensor detects the current ambient pressure after complete pressure equalization and the second pressure sensor no longer detects any flow-related signal.

The process according to the present invention for operating the gas sampling device uses a calibration method for determining the first correction parameter and for calibrating the second pressure sensor designed as a differential pressure sensor. The calibration is used to compensate the effect of ambient pressure on the measuring accuracy of the differential pressure sensor. The ambient pressure brings about a shift of the zero point of the differential pressure sensor. The ambient pressure acting on the differential pressure sensor depends on the site of use, i.e., on the barometric altitude of the site of use, for example, at altitudes above 1,000 m in mountains or in regions near the coast with an altitude of about 100 m, as well as on the current weather situation. These variations at the site of use, which are determined by the location of high-pressure and low-pressure areas, are not predictable and must therefore also be taken into account by a post-calibration at the site of use after the final testing of the device after production. The calibration performed at the time of final testing of the device determines as a first calibration an initial calibration data set with a first initial and a second initial correction parameter $k11$, $k22$ for a preset range of ambient air pressure in combination with the properties of the gas and with the range of vacuum that can be generated by the pump from the current correction parameters $k1$, $k2$ and stores these two initial correction parameters $k11$, $k22$ in an initial calibration data set in a memory in the device.

Following the first calibration, the initial correction parameters $k11$, $k22$ are identical to the current correction parameters $k1$, $k2$ and the initial calibration data set and the current calibration data set are both stored in the memory. These initial calibration values make it possible during the later use of the device to increase the accuracy of the test gas volume being delivered as well as to check the function of the device and to adjust parameter values as well as to analyze the correction parameters determined during the post-calibration. The calibration is performed according to the present invention at at least two calibration points. The first calibration point is the flow-free state at a first pressure level with ambient pressure at the first and second pressure sensors. The at least second calibration point is a flow-free state at a second pressure level at a defined operating vacuum at the first and second pressure sensors. The difference between the differential pressure measured value of the second pressure sensor at the first calibration point and the differential pressure measured value of the second pressure sensor at the second calibration point represents the dependence of the differential pressure measurement of the second pressure sensor on the pressure level prevailing within the gas sampling device. This is a systematic dependence and is defined as a common mode offset, also called "common mode offset," of the second pressure sensor and is stored in the memory as a first correction parameter. This common mode offset represents an essential source of error in respect to the accuracy of the differential pressure measurement. The following example illustrates the error effect. For a first type of a test gas tube, ambient air is drawn at a working point through the test gas tube by means of a pump with a vacuum of 100 mbar. The pump is regulated in the working point to the maintenance of the vacuum level of 100 mbar, so that a flow rate of 2 L per minute is established in this certain type of test gas tube. These 2 L per minute cause a pressure drop of 50 mbar at a laminar flow element. This pressure drop is detected with the second pressure sensor designed as a differential pressure sensor. The laminar flow element comprises in this case two parallel individual tubes of an overall length of about 50 mm with an internal diameter of 0.8 mm each. Another embodiment of the laminar flow element can be designed as being equivalent in terms of construction in respect to the combination of the number of individual tubes, internal diameter of the individual tubes and overall length, a helical winding for reducing the overall length or a splitting of the laminar flow element into a serial arrangement of a plurality of individual elements and is obtained essentially from the boundary conditions of the gas sampling device, which are determined by the design.

If a second type of a test gas tube is operated with the same arrangement, a flow of 0.05 L per minute is established because of a higher flow resistance of the second type at the working point, which equals 100 mbar. This flow of 0.05 liters per minute causes a pressure drop of 1 mbar at the laminar flow element. The typical error of a differential pressure sensor caused by the common mode offset is in the range of 1.5% relative to the pressure level that acts within the gas sampling device on the second pressure sensor. Relative to the working point of 100 mbar selected in this example, this leads to a value of 0.15 mbar. It becomes clear from this that an error effect of 0.15 mbar causes a shift in the attainable measuring accuracy into a range of >10% for the pressure difference of 1 mbar, which drops at the laminar flow element when using the second type of test gas tube.

However, a volume accuracy of <5% is necessary for an accurate and reproducible measurement, and an accuracy requirement of ±0.05 L/min is derived from this for the flow measurement, which in turn leads to a measuring accuracy of <0.05 mbar and a zero point tolerance of 0.02 mbar of the second pressure sensor designed as a differential pressure sensor for the selected arrangement with the laminar flow element comprising two parallel metal tubes of a length of about 50 mm. Measurements have shown that the error effect caused by the common mode offset is a systematic error effect, which depends essentially on the pressure level of the working point and can be systematically eliminated by a calibration at the working point for the measurements that follow during use. The measurements have revealed, furthermore, that the calibration is sufficient at two calibration points, for example, at a first calibration point with ambient pressure in the system and at a second calibration point with 100 mbar vacuum in the system relative to ambient pressure and the common mode offset can be interpolated linearly to a vacuum range from 0 mbar to 300 mbar during use. The different ambient pressure between the calibration point at the time of final testing of the device and the working point during the use of the device has no substantial effect because the device is operated at the calibration point and at the working point in relation to the respective current ambient air pressure. An additional calibration at the site of use may become necessary only in case of operation of the gas sampling device at extremely different altitudes, for example, at sea level or in high mountainous regions above 1,000 m, because the effect of ambient pressure on the housing of the differential pressure sensor has a weak effect on the common mode offset in this case. However, the process according to the present invention for calibrating the gas sampling device with the determination of the common mode offset of the second pressure sensor designed as a differential pressure sensor is also suitable for making it possible to perform an additional calibration at the site of use. An additional effect on the common mode offset arises, in principle, also from the gas and ambient temperatures acting on the pressure sensor. This error effect is avoided already by selecting a suitable differential pressure sensor. A design embodiment for reducing the temperature dependence of a pressure sensor is described in EP 0392486 A1 as well as in DE 3937641 A1. Thus, a temperature difference between the calibration point during final testing of the device and the working point during the use of the device has no effect. Another effect is due to the moisture content of the calibrating gas during final testing of the device and the gas in the measuring environment. This can be compensated by the use of an additional moisture sensor, but it has no effects in reality, because a so-called dry layer is arranged in the vicinity of the gas inlet in most types of test gas tubes, so that the detection reagent in the test gas tube can react with an essentially dry gas. This causes an essentially dry gas to flow through in the gas sampling device, i.e., also through the second pressure sensor designed as a differential pressure sensor. The common mode offset determined during the calibration is thus the essential influencing variable affecting the measuring accuracy and reproducibility of the gas sampling device and can be used for using the gas sampling device during the measuring operation and for testing the ability of the gas sampling device to function. The inclusion of the common mode offset of the second pressure sensor designed as a differential pressure sensor, which said common mode offset was determined during the calibration, is described in a process according to the present invention for operating the gas sampling device and in a process according to the present invention for testing the gas sampling device as another component of the present invention.

The process according to the present invention for calibrating the gas sampling device with determination of the common mode offset of the second pressure sensor designed as a differential pressure sensor will be explained step by step below.

At the beginning of the calibration, the gas sampling device is open at the connection element towards ambient pressure and the pump is stopped in a first step by a control and regulating unit, and a first differential pressure measured value $X2_{D1}$ of the second pressure sensor is subsequently determined and sent to the control and regulating unit.

To check for a flow-free state, the first differential pressure measured value $X2_{D1}$ of the second pressure sensor is checked for variations in a second step. Variations may be monitored, for example, by an analysis of the variance and/or standard deviation, as well as course over time of the variance and/or standard variation. If there are no significant measured value variations, a flow-free state can be assumed. An ambient pressure measured value $X13_A$ is detected now in this flow-free state in a third step by means of the first pressure sensor and sent to the control and regulating unit. This first ambient pressure measured value $X13_A$ represents the ambient air pressure acting at this point in time on the gas sampling device and within the entire gas sampling device on the outside. The gas sampling device is closed on at least one side in a fourth step, so that no convection effects can affect the calibration. A second differential pressure measured value $X2_{D2}$ of the second pressure sensor is detected in a fifth step at a first calibration point, a no-flow state under ambient air pressure, and sent to the control and regulating unit. This second differential pressure measured value $X2_{D2}$ is monitored for variations, the same method being used for monitoring for variations as described in the second step of the calibration process. A first calibration measured value $X1_{K0}$ of the first pressure sensor and a second calibration measured value $X2_{K0}$ are detected in a sixth step and sent to the control and regulating unit. A desired pressure value $Y_{K1}$ for actuating the pump in the second calibration point is determined in a seventh step from the ambient pressure measured value $X13_A$ and the preset vacuum $VP_{K1}$ of, e.g., 100 mbar typical of a measurement with test gas tubes. This desired pressure value $Y_{K1}$ presets the pressure value that is detected in an eighth step in the second calibration point at the outlet of the filter element or at the inlet of the flow resistance (laminar flow element) by the first pressure sensor, and the pump is adjusted to this pressure value for reaching a second pressure level in the second calibration point by means of the control and regulating unit. After reaching the second pressure level as a second calibration point, a testing is performed in the eighth step according to the same method as in the second step as well to determine whether a convection- and flow-free state is present. A third calibration measured value $X1_{K1}$ of the first pressure sensor and a fourth calibration measured value $X2_{K1}$ of the second pressure sensor are detected in this second flow-free state in a ninth step. The fourth calibration measured value $X2_{K1}$ of the second pressure sensor shows, compared with the second calibration measured value $X2_{K0}$ of the second pressure sensor, the dependence of the second pressure sensor on an effect of the pressure level given by the desired pressure value $Y_{K1}$, which effect for the value pair $X1_{K1}, X2_{K1}$ at a second pressure level of 100 mbar in this case is below the first pressure level ambient pressure, given by the value pair $X1_{K0}, X2_{K0}$. The difference $X2_{K0}-X2_{K1}=X2_{Bias\_1-0}$ indicates as a first common mode value $X2_{Bias\_1-0}$ the common mode offset of the second pressure sensor, which is caused by an identical change of the pressure difference from the ambient pressure on the two connection sides of the second pressure sensor, which said pressure difference is caused by the vacuum. An additional third calibration point can be optionally approached in the eighth step with a third pressure level by performing the procedure for reaching the third pressure level in the same manner as was described for the second calibration point, with the difference that a third pressure level of, for example, 300 mbar, which differs from the second pressure level, is approached and a third value pair $X1_{K2}, X2_{K2}$ is detected and a second common mode value $X2_{Bias\ 2-0}$ is determined. The calibration measured values $X2_{Bias\ 1-0}, X2_{Bias\ 2-0}$ (common mode values, common mode offset) of the second pressure sensor are converted in a tenth step with the calibration measured values $X1_{K0}, X1_{K1}, X1_{K2}$ of the first pressure sensor into a functional relationship as an inphase amplification or common mode gain or bias $G_{Bias}=(X2_{K0}-X2_{K1})/(X1_{K0}-X1_{K1})$. Such a functional relationship can be determined on the basis of the calibration measured values in a suitable manner by means of a compensation function, for example, by linear or nonlinear interpolation. The inphase amplification $G_{Bias}$ as a first correction parameter k1 in the calibration data set is entered into the memory for further use in an eleventh step. After entering the calibration data set in the memory in the eleventh step, the pump is switched off and the calibration is ended.

In an optional expansion of the calibration process, the calibration is continued according to the present invention at the end of the calibration as an expanded calibration with further steps in order to determine the initial second correction parameter k22 or current second correction parameter k2. The closed connection element is again released for this in the twelfth step and a testing test gas tube with known properties and/or properties in a typical predetermined range, for example, in a range of 0.25 L per minute to 0.300 L per minute at a pressure difference of 100 mbar is connected to the connection element of the gas sampling device. The pump is subsequently switched on again in the thirteenth step and by observing the measured values of the second pressure sensor, in comparison with the desired value of the calibration point, on the one hand, but also by analysis of the variations of the measured values, one waits until the previous calibration point is again adjusted in a stable manner. To detect the curve describing the drop curve, the pump is then switched off at the calibration point in a fourteenth step and the pressure signal of the first pressure sensor and the differential pressure signal of the second pressure sensor are detected and continuously recorded. If the pressure value drops below a first threshold value of the pressure signal of the first pressure sensor, this differential pressure signal is converted by means of the pressure-vs.-flow characteristic of the laminar flow element into a flow value in a fifteenth step during the duration of the drop curve and is integrally summed up continuously into a volume until the pressure value drops below a second threshold value of the pressure signal of the first pressure sensor. This determined volume is related in a sixteenth step to a typical volume of the gas sampling device and a second correction factor k2 is determined from this. This second correction parameter k2 is stored in the memory. The typical volume present in the gas sampling device consists essentially of the buffer volume and is known for a typical arrangement. The typical volume can also be determined additionally accurately during a final testing of the gas sampling device by means of an accurate flow measurement. The threshold values can be set and standardized in a suitable manner analogously to the definition of a so-called drop time constant $T_{90\text{-}10}$. When determining a $T_{90\text{-}10}$ drop time constant, the duration during which a signal has decreased from 90% of a signal value to 10% of the value is determined. In another suitable manner, the measured values of the pressure sensor designed as a differential pressure sensor are smoothed and measured value freak values and noises are eliminated. Both statistical and mathematical methods and/or analog filter circuits and/or digital filter circuits are available for this. The calibration with the steps one through twelve or with the steps one to seventeen with the determination of the first and second correction parameters k1, k2 is performed for the first time at the time of the final testing of the device after production and the first and second correction parameters k1, k2 determined are stored in the memory separately in an initial calibration data set as a first initial correction parameter k11 and as a second initial correction parameter k22. In many applications, the calibration is performed as a post-calibration before each measurement in those cases in which a calibration is made necessary by a change in the air pressure conditions beyond the range of ambient air pressure, which range was taken into account within the framework of the first-time calibration, or if a change of components is determined in case of a system check initiated automatically by the gas sampling device or by the user and/or if a replacement of components or cleaning of components, for example, of the laminar flow element, must be performed in the course of maintenance operations.

In the cases of post-calibration, an additional current calibration data set with current correction parameters k1, k2 is stored in the memory separately besides the initial calibration data set. Information can then be obtained on the ability of the gas sampling device to function after the post-calibration from a comparison of the correction parameters k1 with k11 and of k2 with k22 and the measuring operation can be continued with the use of the current correction parameters in case of minor differences between the initial and current correction parameters, and in case of significant deviations between initial and current correction parameters, the user is notified of the deviation determined by a corresponding error message.

The process according to the present invention for operating the gas sampling device during the measuring operation uses the calibration data sets determined during the calibration with the first correction parameter for compensating the error effects on the differential pressure sensor, which are caused by pressure. The course of the process according to the present invention for the measuring operation of the gas sampling device is explained in more detail below.

At the beginning of the measuring operation, the pump is stopped in a first step by the control and regulating unit and a first differential pressure measured value $X2_{D1}$ of the second pressure sensor is detected and sent to the control and regulating unit. A checking is subsequently performed in a second step on the basis of the first differential pressure measured value $X2_{D1}$ to determine whether a flow-free state is present in the arrangement. An ambient pressure measured value $X1_A$ of the first pressure sensor is detected in a third step by means of the first pressure sensor in a first mode of operation in the presence of a flow-free state and sent to the control and regulating unit. A desired pressure value is set at $Y_S = X1_A - VP_{Tube}$ in the next, fourth step on the basis of the ambient pressure measured value $X1_A$ and an operating vacuum value $VP_{Tube}$ typical of the test gas tube being used. In the next, fifth step, the control and regulating unit switches the pump into delivery operation and adjusts it to the desired pressure value $Y_S$ by current measured values $X1_{M1}$ through $X1_{Mn}$ being then detected in a sixth step in a continuous, repeated sequence of the following steps six through ten and being sent to the control and regulating unit, and by the control and regulating unit determining in a seventh step a control deviation from the desired pressure value $Y_S$ and the current pressure sensor measured value of the first pressure sensor $X1_{Mn}$ and regulating the pump such that the remaining control deviation be as low as possible. Measured values $X2_{DM1}$ through $X2_{DMn}$ are detected as pressure differences by the second pressure sensor in an eighth step. These measured values through $X2_{DMn}$ are converted by means of the inphase amplification $G_{Bias}$ determined during the calibration into differential pressure measured values $X22_{DMn} = X2_{DMn} - G_{Bias}$ freed from the common mode offset, which are freed from the common mode offset and hence from the pressure effect of the desired pressure $Y_S$ on the differential pressure measurement. The pure differential pressure measured values $X22_{DMn}$ are subsequently converted in a ninth step into flow values $XF_n$ 51 related to standard conditions (1,013 mbar at 20° C.) based on a pressure-vs.-flow characteristic of the laminar flow element, including the current ambient conditions temperature and air pressure. The standardized flow values $XF_n$ 51 determined in a continuous sequence are integrally cumulated into a standard admitted gas volume XV 39 in a next, tenth step.

The cumulated standard admitted gas volume XV 39 is compared in an eleventh step with a desired volume YV 36 typical of the test gas tube being used and the measuring operation is terminated by the pump being stopped by the control and regulating unit as soon as the cumulated standard admitted gas volume XV 39 has exceeded the desired volume YV 36. Besides the embodiment of the gas sampling device according to the present invention with a first pressure sensor and a second pressure sensor, a third barometric pressure sensor, which is additionally present in the arrangement and has a connection to the ambient air pressure, may be provided for detecting the current ambient air pressure in an alternative embodiment of the process for calibrating the gas sampling device and process for operating the gas sampling device.

This sensor may be both connected to the gas guide at the connection element via a connecting piece and also arranged without any connection with the gas guide separately, for example, within the device housing and be connected by its port with the ambient air pressure. The ambient air pressure is detected by means of this third sensor in this alternative embodiment, so that the first pressure sensor is not used to detect ambient air pressure and the monitoring of the flow-free state in the second step can be omitted as well.

In an especially preferred embodiment of the process for operating the gas sampling device, a variant is provided in the process control, in which the determination of the current ambient air pressure is performed only once in a second mode of operation for measuring a plurality of test gas tubes within one measurement series and the desired pressure values used for the different types of test gas tubes are derived therefrom for the actuation of the pump.

To carry out a measurement series with a plurality of test gas tubes at the same site of use at equal barometric altitude, it is not necessary to take into account the current air pressure each time before each new test gas tube is connected. The second mode of operation, which comprises a corresponding variation of the process control during the operation of the gas sampling device, is to be selected for this by the user. Contrary to this, the first mode of operation is to be selected by the user for a measurement series with a plurality of measurements following each other at short intervals of time if a first measurement is performed on the first floor of a multi-story building at sea level and measurement is continued on the fiftieth floor (approximately 100 m) of the same building the measurement being taken within a few minutes. The pressure difference from a value of 1,013 mbar at 20° C. from the first floor to the fiftieth floor is already more than 10 mbar for such a difference in altitude. These 10 mbar must also be taken into account when regulating the pump, because the gas sampling device would otherwise be operated with a vacuum of only 90 mbar relative to the environment instead of, for example, 100 mbar vacuum, which would lead to a distortion of the entire measurement both when the pump is actuated to reach the desired pressure level and concerning the conversion into the standard admitted gas volume. It is therefore necessary in such a case to take into account the current air pressure by means of the first or third pressure sensor in the measurement process in every case.

The gas sampling device is tested in another preferred embodiment of the process for operating the gas sampling device. The testing of the gas sampling device takes place during the operation optionally at the end of a measuring operation and is used to detect a change in the properties of the gas or in the properties of the laminar flow element during the operation. By means of such a testing, the second correction parameter k2 can be determined anew at the end of every measurement or after a predetermined and monitored number of measurements, where the number of said measurements is detected, and it is compared with the correction parameter stored in the memory, which said parameter is entered in said memory last, and/or with the initial second correction parameter. The process of testing the gas sampling device subsequent to a measurement during the operation corresponds, as far as the process is concerned, to the process of the expanded calibration. A curve of the differential pressure signal of the second pressure signal is analyzed here in order to detect a change in the properties of the laminar flow element, which change developed after the last calibration. This change is entered in the memory as a current second correction parameter k2 in the calibration data set. A cause of a change in the property of the laminar flow element is present, for example, if the flow resistance of said laminar flow element is increased by an impurity. Besides the effect of an increased flow resistance during the determination of the volume flow from the differential pressure signal of the second pressure sensor, an increased flow sensor also affects the quality of the differential pressure signal of the second pressure sensor itself. Thus, even an insignificantly increased flow resistance will already affect the common mode offset of the second pressure sensor. As a result of the performance of the process of testing the gas sampling device, it may be necessary in such a case to determine a current common mode offset of the second pressure sensor and to update the first correction parameter in the memory. Another cause of a change in the properties of the laminar flow element compared with the last use, the calibration or the last testing is given if the viscosity of the carrier gas has changed. This happens, for example, when the gas sampling device had been used for a measurement in ambient air and will be used in the next application to detect a trace gas in an industrial carrier gas. If measurement is carried out, for example, in hydrogen as the carrier gas, hydrogen has a viscosity of about $9*10-6$ Ns/m$^2$ under standard conditions (25° C., 1,013 mbar, dry gas). The difference from the viscosity of ambient air, equaling approximately $19*10^{-6}$ Ns/m$^2$ under standard conditions, equals a factor of about 2 in this case. The gas sampling device is to be recalibrated to the carrier gas in such a case. If the testing performed at the end of a measurement determines a changed state of flow, the measurement is to be discarded and the user shall perform a check, for example, to determine the gas in which the previous measurement was performed and recalibrate the gas sampling device correspondingly to the current measurement task. Due to the fact that contamination of the laminar flow element is recognizable in such a process for testing the gas sampling device, it is possible to correspondingly inform the user of the quality of the measurement at the end of the measurement, or to discard the measured value determined if major deviations are recognized between the properties of the laminar flow element during the operation on site compared to a previous calibration, for example, a first calibration performed before the gas sampling device had been shipped, and to display this to the user as corresponding information in the form of an optical or acoustic display. To detect such a change in the properties of the laminar flow element or in the properties of the gas, provisions are made according to the present invention for detecting the time curve of the dropping differential pressure signal of the second pressure signal after switching off the pump at the of end of the measurement. Unlike in the process of the expanded calibration, no special testing test gas tube is used here, but the test gas tube with which the measurement had been carried out before during the operation is used.

The gas sampling device is tested for this according to the present invention at the end of the measurement with the test gas tube connected to switching off of the pump in the same manner as in case of the expanded calibration at the end of the calibration. The pattern of the drop curve of the differential pressure signal of the second pressure sensor is analyzed here in a similar manner in order to detect a change that occurred in the properties of the laminar flow element after the last calibration and to enter it in the memory as a current second correction parameter k2. To test the gas sampling device at the end of the measuring operation, the measuring operation is continued with further steps in order to determine the current second correction parameter k2. To detect the drop curve, the pressure signal of the first pressure signal and the differential pressure signal of the second pressure sensor are then detected and continually recorded with the pump switched off in a twelfth step with the test gas tube continuing to be connected. If the value of the pressure signal of the first pressure signal drops below a first threshold value during the duration of the drop curve, this differential pressure signal is converted by means of the pressure-vs. flow characteristic of the laminar flow element into a flow value and summed up integrally continuously until the value drops below a second threshold value of the pressure signal of the first pressure sensor. This determined volume is related in a thirteenth step to a typical volume of the gas sampling device and a second correction factor k2 is determined, and the second correction parameter k2 is stored in the memory. In an optional fourteenth step, the initial second correction parameter k22 is compared with the current second correction parameter k2 and a message is sent to the operating and output unit in case a predetermined deviation of the current second correction parameter k2 is exceeded by the initial second correction parameter k22. The first pressure sensor can be used in the embodiments of the process according to the present invention for operating the gas sampling device to detect the current ambient air pressure if the pump is switched off in the third step and the first pressure sensor is in direct connection with the ambient air pressure, i.e., the gas sampling device is open towards the environment, while the connection element or gas outlet element is not closed, so that the ambient air pressure is present at the first pressure sensor.

Some exemplary embodiments of the present invention will be explained in more detail below on the basis of the drawings. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
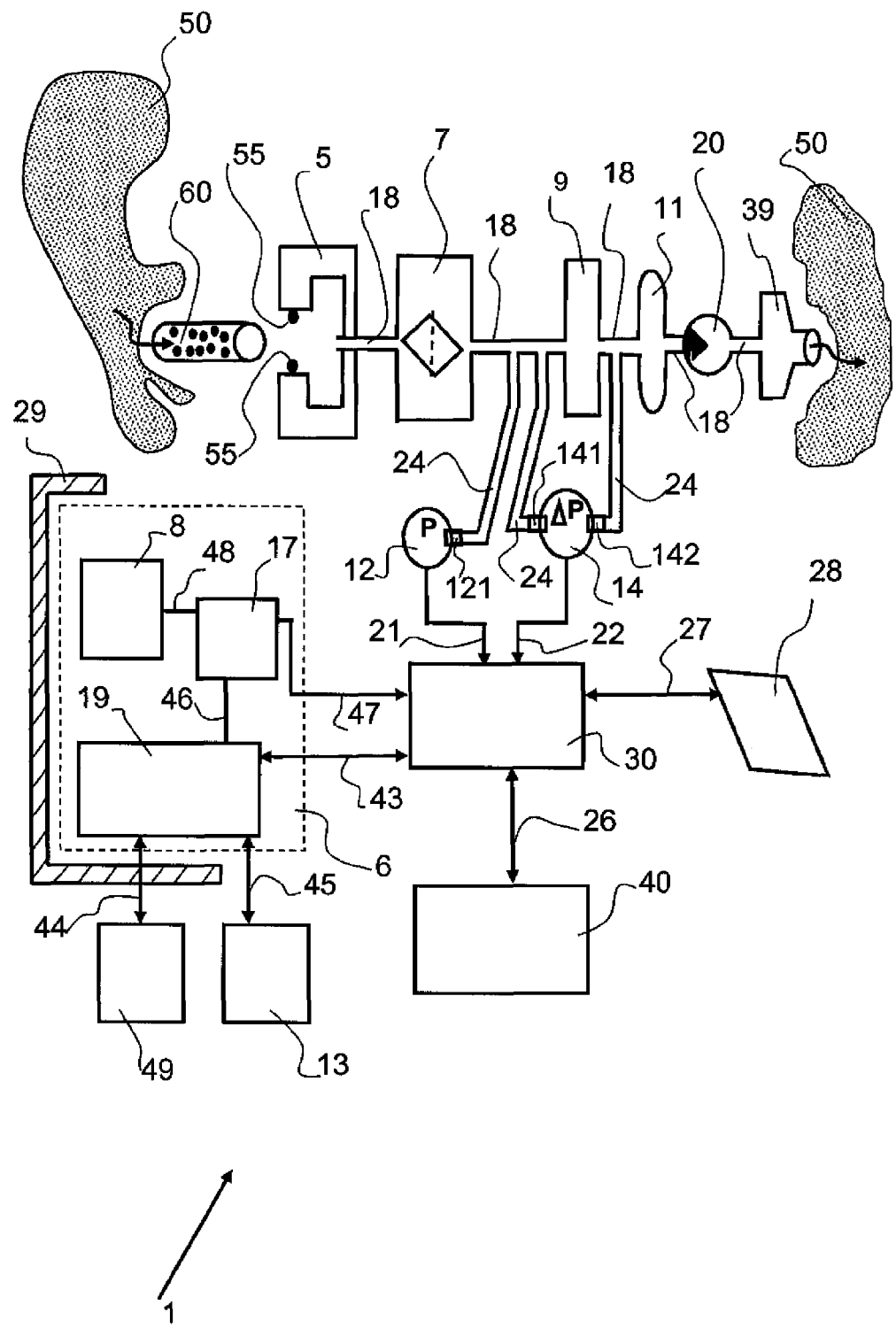
FIG. 1 is a view of the components of a first gas sampling device for colorimetric gas analysis.

Referring to the drawings in particular, FIG. 1 shows a first gas sampling device 1 according to the present invention in a symbolic view of the components.

The first gas sampling device 1 comprises a connection element 5 for connecting with a test gas tube 60, a filter element 7, a flow resistance designed as a laminar flow element 9, a buffer volume 11, a first pressure sensor 12, a second pressure sensor 14, a pump 20 and a gas outlet element 39. The connection element 5, filter element 7, as laminar flow element 9, buffer volume 11, pump 20 and gas outlet element 39 are pneumatically connected to one another via connection lines. Further components are a control and regulating unit 30, a memory 40, a data interface 19, an energy supply unit 17 and an operating and output unit 28. The test gas tube 60 shown symbolically is not a part of the first gas sampling device 1 and is shown here for illustration only. The control and regulating unit 30 is connected to the energy supply unit 17 via a first supply line 47. To exchange status data, the energy supply unit 17 is connected to the data interface 19 via a sixth data connection 46. The control and regulating unit 30 is designed to keep ready data, for example, status reports, for example, an energy supply status, status of the energy supply unit 17, of pressure sensors 12, 14, of pump 20, of filter element 7 or of laminar flow element 9, as well as signals of pressure sensors 12, 14 and to exchange them unidirectionally or bidirectionally with the testing means 49 necessary for the final testing or calibration via a fourth data connection 44 via the data interface 19 connected by means of a third data connection 43. The testing means 49 is connected to the data interface 19 with a fifth data line 44. The fourth data line 44 may also connect the testing means 49 directly to the data interface 19, but additional data transmission elements, such as wired (LAN) or wireless (WLAN) networks may also be provided and arranged as components of the data interface 19 and of the fourth data line 44 in the gas sampling device 1, so that a remote-controlled status detection or calibration is possible. In a special variant, the data interface 19 is designed as a wireless interface, for example, as a telemetric, optical or inductive interface. The data interface 19 is designed in another, special manner to read in specific data of the test gas tubes by means of a connected reading device 13 via a fifth data connection 45. Such a reading unit 13 may be, for example, a reader for bar codes or radio frequency identification (RFID) and be both a part of the gas sampling device 1 and connected as an external device to the gas sampling device 1 via the data interface 19. The test gas tubes 60 or packing of the test gas tubes 60 contains corresponding identification elements, such as bar codes or RFID transponders in such a case. The energy supply unit 17 is preferably designed as a battery in case of a gas sampling device 1 designed as a mobile hand-held device, in which case both primary batteries and rechargeable batteries (storage batteries) are suitable for mobile use. However, connection of an external power pack 8 via a second supply line 48 is also provided for directly supplying the gas sampling device 1 and/or charging the rechargeable batteries for a temporary stationary use. Such a power pack 8 is of an inductive design in a suitable manner in a special variant according to this FIG. 1. The data interface 19 with power supply unit 17 and with power pack 8, as well as with an inductive charging and holding element 29 are thus arranged combined in an energy charging and interface device 6, so that an exchange of data between gas sampling device 1 with testing means 49 is made possible in a combined manner with the supply of gas sampling device 1 with electric energy, without additional electric connections being necessary. The control and regulating unit 30 is designed to exchange data unidirectionally or bidirectionally with operating and output unit 30. The data may contain, on the one hand, instructions for use or error messages of the control and regulating unit 30, which are displayed on the operating and output unit 28, and, on the other hand, user actions, such as typing data of the test gas tubes 60, start, stop or interruption of a measurement, of a self-test or a calibration must be sent from operating and output unit 28 to control and regulating unit 30. In a simplest embodiment, the operating and output unit 28 comprises a plurality of individual input and display elements, designed, for example, as mechanical-electric switching elements and status LEDs. However, the operating and output unit 28 may also be designed in the form of a numeric or alphanumeric keyboard in combination with an LED or LCD display, or even as a touch-sensitive input and display element (touch screen). The first pressure sensor 12 is designed as an absolute pressure sensor, which is connected to a first measuring connection 121 at the outlet of the filter element 7 and/or at the inlet of the laminar flow element 9 and detects an absolute pressure which is present there. The second pressure sensor 14 is designed as a differential pressure sensor, which is connected to the laminar flow element 9 both on the inlet side with a second measuring connection 141 and on the outlet side with a third measuring connection 142. The second pressure sensor 14 detects a pressure difference present over the laminar flow element 9. The first and second pressure sensors 12 and 14 as well as the measuring connections 121, 141, 142 thereof are connected to the connection lines 18 via measuring lines 24. A first signal line 121 connects the first pressure sensor 12 electrically to the control and regulating unit 30. Second and third signal lines 141, 142 connect the second pressure sensor 12 electrically to the control and regulating unit 30. The first and second pressure sensors 12, 14 are connected to the control and regulating unit 30 via measuring lines 24. Memory 40 is connected to the control and regulating unit 30 via a first data connection 26. A second data line 27 connects the control and regulating unit 30 to the operating and output unit 28. The operating and output unit 28 enables the user to make a selection from different modes of operation of the gas sampling device 1. Thus, a mode for calibration, at least a first mode for the measuring operation and a mode for testing the gas sampling device 1 are provided. The modes for the measuring operation of the gas sampling device 1 are used for adaptation to the type of the test gas tube 60 being used; for example, pump 20 can thus be operated at a pressure level of 100 mbar below ambient pressure in a first measuring operation mode, and pump 20 can be operated, for example, at a pressure level of 300 mbar below ambient pressure in a second measuring operation mode. Another measuring operation mode is provided for an expedited performance of a measurement series, in which the interval between operating steps is shortened to the extent that detection and inclusion of the ambient air pressure and/or even of the humidity of the ambient air and/or of the ambient temperature are performed only once at the start of the measurement series in the measuring operation mode for performing the measurement series. A quantity of gas to be measured is drawn by pump 20 from the measuring environment 50 via connection element 5 through test gas tube 60. Test gas tube 60 is connected to connection element 5 gas-tightly by means of sealing elements 55. The quantity of gas being delivered flows in a serial arrangement at first through test gas tube 60, then filter element 7, laminar flow element 9, then buffer volume 11, subsequently pump 20 and returns into the measuring environment through gas outlet element 39.

Figure 2:
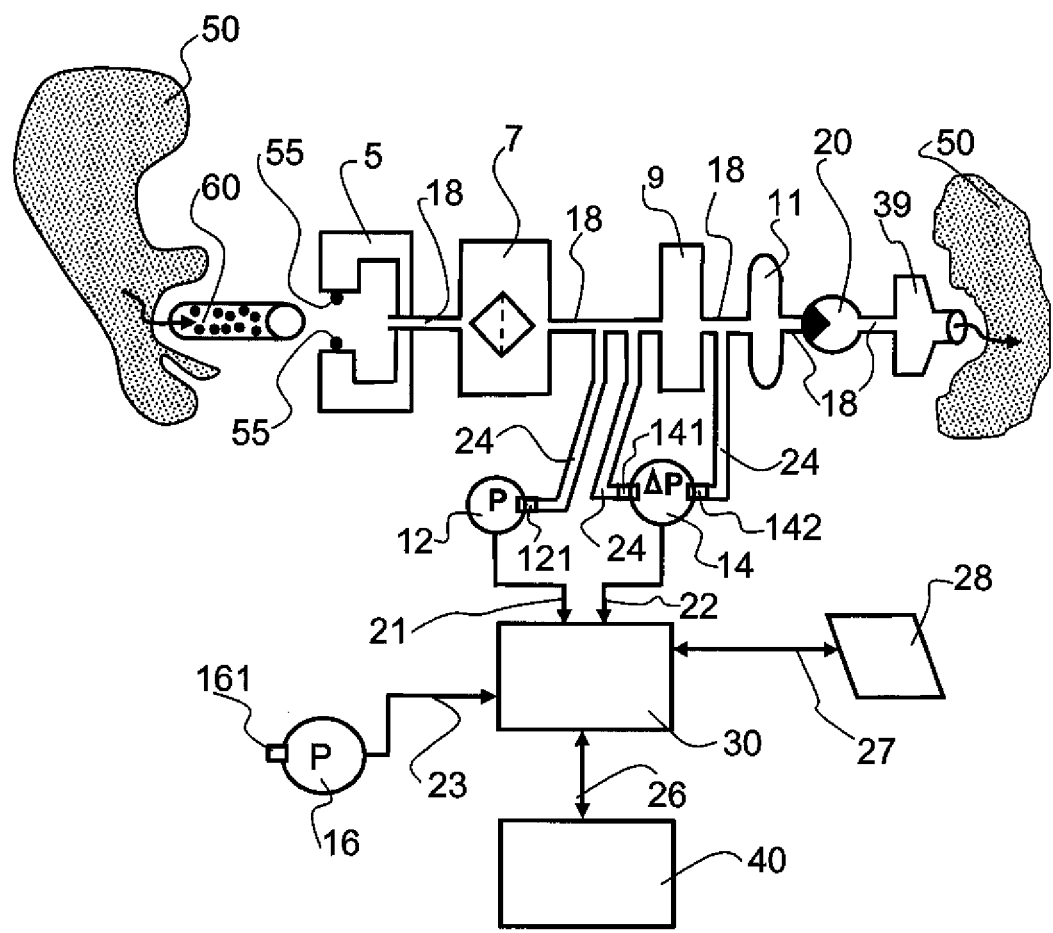
FIG. 2 is a view of the components of an alternative gas sampling device for colorimetric gas analysis.

FIG. 2 shows a second gas sampling device 10 according to the present invention in a symbolic view of the components.

The second gas sampling device 10 comprises a connection element 5 for connecting to a test gas tube 60, a filter element 7, a flow resistance designed as a laminar flow element 9, a buffer volume 11, a first pressure sensor 12, a second pressure sensor 14, a pump 20 and a gas outlet element 39. The connection element 5, the filter element 7, the laminar flow element 9, the buffer volume 11, the pump 20 and the gas outlet element 39 are pneumatically connected to one another via connection lines 18. The test gas tube 60 shown symbolically is not part of the second gas sampling device 10 and is shown here for illustration only. Further components are a control and regulating unit 30, a memory 40 and an operating and output unit 28. A third pressure sensor 16, which is connected to the measuring environment 50 by means of a fourth measuring connection, is provided as another component of the second gas sampling device. The first pressure sensor 12 is designed as an absolute pressure sensor, which is connected to a first measuring connection 121 at the outlet of the filter element 7 and/or at the inlet of the laminar flow element 9 and detects an absolute pressure which is present there. The second pressure sensor 14 is designed as a differential pressure sensor, which is connected to the laminar flow element 9 both on the inlet side with a second measuring connection 141 and on the outlet side with a third measuring connection 142. The second pressure sensor 14 detects a pressure difference present over the laminar flow element 9. The first, second and third pressure sensors 12, 14, 16 and the measuring connections 121, 141, 142, 161 thereof are connected to the connection lines 18 via measuring lines 24. A first signal line 121 connects the first pressure sensor 12 electrically to the control and regulating unit 30. Second and third signal lines 141, 142 connect the second pressure sensor 12 electrically to the control and regulating unit 30. A fourth signal line 161 connects the third pressure sensor 16 electrically to the control and regulating unit 30. Memory 40 is connected to control and regulating unit 30 via a first data line 26. A second data line 27 connects the control and regulating unit 30 to the operating and output unit 28. Thus, a mode for calibration, at least a first mode for the measuring operation and a mode for testing the gas sampling device 10 are provided. The measuring operation modes of the gas sampling device 10 are used for adaptation to the type of the test gas tube 60 being used; pump 20 can thus be operated in a first measuring operation mode at a pressure level of 100 mbar below ambient pressure, and pump 20 ban be operated at a pressure level of 300 mbar below ambient pressure in a second measuring operation mode. Another measuring operation mode is provided for the expedited performance of measurement series, in which case the interval between operating steps is reduced to such an extent that detection and inclusion of the ambient air pressure and/or also of the humidity of the ambient air and/or ambient temperature are performed only once at the start of the measurement series in the measuring operation mode for performing measurement series. A quantity of gas to be measured is drawn by pump 20 via connection element 5 through test gas tube 60. Test gas tube 60 is connected to connection element 5 gas-tightly by means of sealing elements 55. The quantity of gas being delivered flows in a serial arrangement at first through test gas tube 60, then filter element 7, laminar flow element 9, then buffer volume 11, subsequently pump 20 and returns into the measuring environment through gas outlet element 39.

Figure 3A:
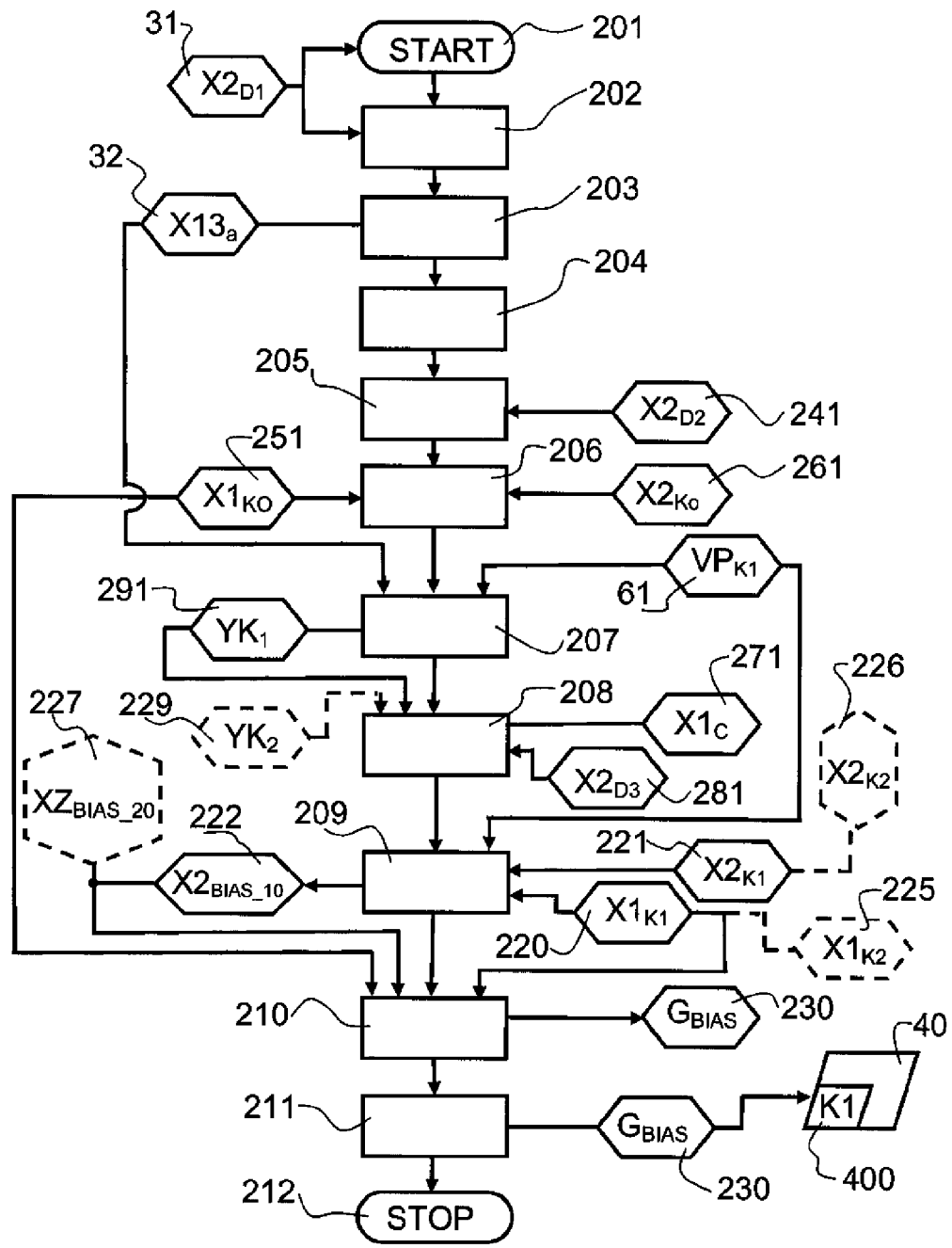
FIG. 3a is a first flow chart for calibrating the first gas sampling device.

FIG. 3a shows a first flow chart for calibrating the first gas sampling device 1 according to FIG. 1. A sequence of eleven calibration steps illustrates the calibration process according to the present invention in detail. The process takes place in the following manner:

a) With the connection element 5 open towards the measuring environment 50 (FIG. 1), a pump 20 (FIG. 1) is stopped by a control and regulating unit 30 (FIG. 1) in a first calibration step 201 at the beginning and a first differential pressure measured value $X2_{D1}$ 31 of a second pressure sensor 14 (FIG. 1) is detected and sent to a control and regulating unit 30 (FIG. 1), b) a check is performed in a second calibration step 202 on the basis of the first differential pressure measured value $X2_{D1}$ 31 to determine whether a flow-free state is present in the gas sampling device, c) an ambient pressure measured value $X13_A$ 32 is detected in a third calibration step 203 in the presence of a flow-free state by means of a first pressure sensor 12 (FIG. 1) and sent to the control and regulating unit 30 (FIG. 1), d) the device is closed in a fourth calibration step 204 at least on one side at the connection element 5 (FIG. 1), so that a convection- and flow-free state is present, e) a second differential pressure measured value $X2_2$ 241 of the second pressure sensor 14 (FIG. 1) is detected in a fifth calibration step 205 at a first calibration point and sent to the control and regulating unit 30 (FIG. 1), and the second differential pressure measured value $X2_{D2}$ 241 is monitored for variations and the convection- and flow-free state is checked, f) a first calibration measured value $X1_{K0}$ 251 of the first pressure sensor 12 (FIG. 1) and a second calibration measured value $X2_{K0}$ 261 of the second pressure sensor 14 (FIG. 1) are detected at the first calibration point in a sixth calibration step 206 and sent to the control and regulating unit 30 (FIG. 1), g) a first desired calibration pressure value $Y_{K1}$ 291 is determined in a seventh calibration step 207 from the ambient pressure value $X13_A$ 32 determined in the third calibration step and from a first vacuum value $VP_{K1}$ 61 by forming the difference with $Y_{K1}=X13_A-VP_{K1}$, h) a pressure measured value of the first pressure sensor 12 (FIG. 1) is detected as a control pressure value $X1_c$ 271 in an eighth calibration step 208 and pump 20 (FIG. 1) is actuated by control and regulating unit 30 (FIG. 1) such that the closed space between connection element 5 (FIG. 1) and pump 20 (FIG. 1) is evacuated to the extent that the control pressure value $X1_c$ 271 reaches a first desired calibration pressure value $Y_{K1}$ 291, pump 20 (FIG. 1) is stopped when the first desired calibration pressure value $Y_{K1}$ 291 is reached, a third differential pressure measured value $X2_{D3}$ 281 of the second pressure sensor 14 (FIG. 1) is detected, checked for variations, and a convection- and flow-free state is thus checked, i) a third calibration measured value $X1_{K1}$ 220 of the first pressure sensor 12 (FIG. 1) and a fourth calibration measured value $X2_{K1}$ 221 of the second pressure sensor 14 (FIG. 1) are detected in a ninth calibration step 209 and a first common mode offset $X2_{Bias\_1-0}$ 222 is formed from the difference $X2_{Bias\_1-0}=X2_{K0}-X2_{K1}$ from the first $X2_{K0}$ 261 and fourth calibration measured value $X2_{K1}$ 221, j) an inphase amplification $G_{Bias}$ 230 is formed by $G_{Bias}=(X2_{K0}-X2_{K1})/(X1_{K0}-X1_{K1})$ in a tenth calibration step 210, and k) in an eleventh calibration step 211, the relationship between the common mode values $X2_{Bias}$ of the second pressure sensor 14 (FIG. 1) and calibration measured values $X1_{Kn}$ of the first pressure sensor 12 (FIG. 1) and inphase amplification $G_{Bias}$ 230 is stored in the memory 40, for example, in the form of a table or in the form of a functional relationship in a first calibration data set k1 400 and the calibration has come to an end 212.

The pump can be optionally actuated towards a second desired calibration pressure value $Y_{K2}$ 229 in the eighth calibration step 208 and adjusted to a pressure level corresponding to the second desired calibration pressure value $Y_{K2}$ 229 by means of a control pressure value $X1_c$ 271 detected by the first pressure sensor, and a third value pair with a fifth calibration measured value $X1_{K2}$ 225 and a sixth calibration measured value $X2_{K2}$ 226 can be detected in the next, ninth calibration step 209, and a second common mode value $X2_{Bias\_2-0}$ 227 can be formed from the difference $X2_{Bias\_2-0}=X2_{K0}-X2_{K2}$. The values $Y_{K2}$ 229, $X2_{K2}$ 226, $X_{K2}$ 225, $X2_{Bias\_2-0}$ 227, which are additionally included in the process and used in this optional manner, are shown in FIG. 3a by broken contour lines and action lines.

Figure 3B:
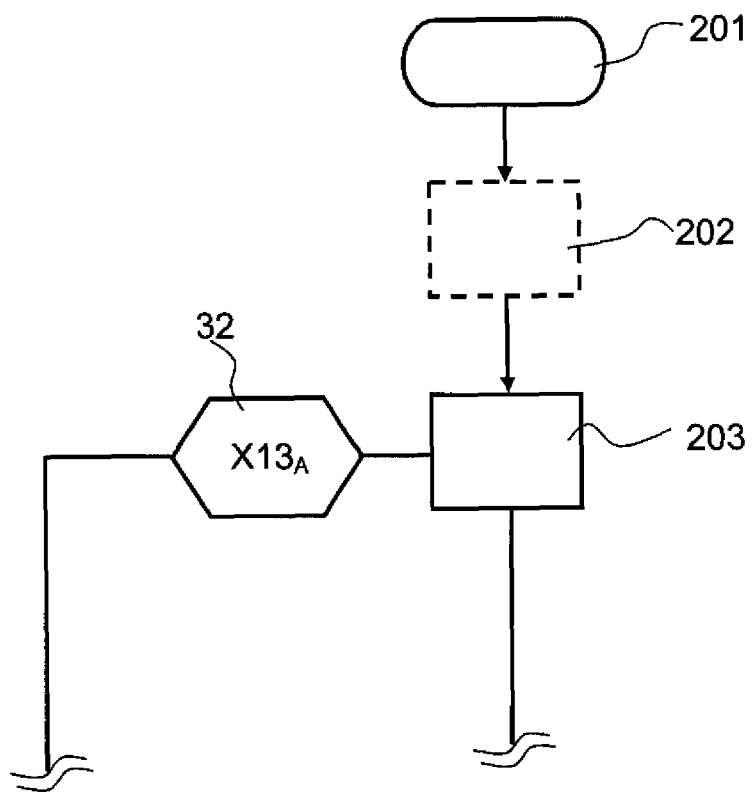
FIG. 3b is a second flow chart for calibrating the first or alternative gas sampling device.

FIG. 3b shows a second flow chart for calibrating the second gas sampling device 10 according to FIG. 2 and the first gas sampling device 1 according to FIG. 1.

The second flow chart for calibration according to this FIG. 3b takes into account the fact that an additional, third pressure sensor 16 (FIG. 2) is available for the measurement of ambient air in the gas sampling device 10 (FIG. 2).

Furthermore, this second flow chart for calibrating the first gas sampling device 1 according to FIG. 1 can be advantageously used to save time in a calibration cycle, because the ambient pressure does not change so substantially during the duration of the calibration series in a series of calibrations that are carried out at short time intervals one after another that the ambient pressure would have to be detected anew, but it is to be determined at the time of the first calibration only within the calibration series.

The process corresponds essentially to the flow chart according to FIG. 3a. The flow chart according to this FIG. 3b is explained in more detail by highlighting the differences from FIG. 3a. The first three calibration steps of a sequence of twelve calibration steps are shown; the calibration steps from calibration step four to calibration step twelve correspond identically to the course of the calibration of the gas sampling device according to the first flow chart according to FIG. 3a for calibrating the gas sampling device and are not shown additionally in FIG. 3b. The process takes place in the following manner:

a) With the connection element 5 (FIG. 1) open towards the measuring environment 50 (FIG. 1), a pump 20 (FIG. 2) is stopped by a control and regulating unit 30 (FIG. 2) in a first calibration step 201 at the beginning of the measuring operation, b) the second calibration step with the checking for a flow-free state is omitted in the flow chart, and c) an ambient pressure measured value $X13_A$ 32 is detected in a third calibration step 203 by means of a third pressure sensor 16 (FIG. 2) and sent to the control and regulating unit 30 (FIG. 2).

The following calibration steps four 204 through twelve 212 correspond to the course of calibrating the gas sampling device according to the first flow chart according to FIG. 3a for calibrating the gas sampling device.

Figure 4A:
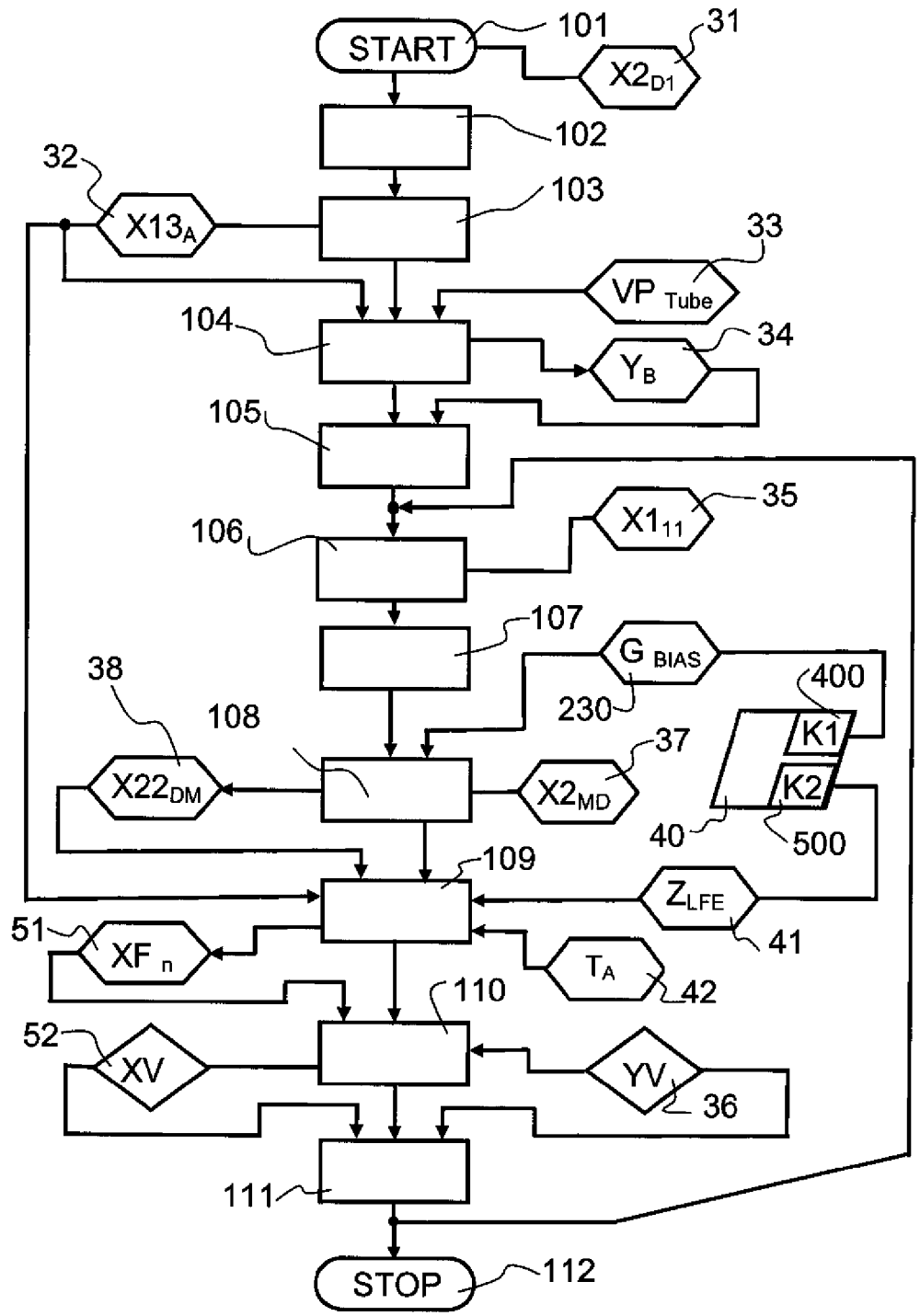
FIG. 4a is a first flow chart for operating the first gas sampling device.

FIG. 4a shows a flow chart for operating the first gas sampling device 1 according to FIG. 1. The process according to the present invention for operating a gas sampling device is described here by a sequence of eleven operating steps with a continuous repetition of the operating steps six through eleven.

The process is carried out in such a way that a) with the connection element 5 (FIG. 1) open towards the measuring environment 50 (FIG. 1), a pump 20 (FIG. 1) is stopped by a control and regulating unit 30 (FIG. 1) in a first operating step 101 at the beginning of the measuring operation and a first differential pressure measured value $X2_{D1}$ 31 of a second pressure sensor 14 (FIG. 1) is detected and sent to a control and regulating unit 30 (FIG. 1), b) a check is performed in a second operating step 102 on the basis of the first differential pressure measured value $X2_{D1}$ 31 to determine whether a flow-free state is present in the gas sampling device, c) an ambient pressure measured value $X13_A$ 32 is detected by means of a first pressure sensor 12 (FIG. 1) in a third operating step 103 in the presence of a flow-free state and sent to the control and regulating unit 30 (FIG. 1), d) a first desired operating pressure value $Y_B$ 34 is determined from the difference $Y_B = X1_A - VP_{Tube}$ of the ambient pressure measured value $X13_A$ 32 and a first desired vacuum value $VP_{Tube}$ 33 and set in a fourth operating step 104 on the basis of the ambient pressure measured value $X13_A$ 32 and a desired vacuum value $VP_{Tube}$ 33 typical of the test gas tube 60 (FIG. 1) to be used, e) control and regulating unit 30 (FIG. 1) switches pump 20 (FIG. 1) into a delivery operation in a fifth operating step 105, f) a third pressure measured value $X1_M$ 35 is detected by means of the first pressure sensor 2 (FIG. 1) in a sixth operating step 106 and sent to the control and regulating unit 30 (FIG. 1), g) in a seventh operating step 107, control and regulating unit 30 (FIG. 1) regulates pump 20 (FIG. 1) on the basis of the desired operating pressure value $Y_B$ 34 and the third pressure measured value $X1_M$ 35 such that the desired operating pressure value $Y_B$ and the third pressure measured value $X1_M$ 35 agree, h) differential pressure measured values $X2_{MDn}$ 37 are detected by the second pressure sensor 14 (FIG. 1) in an eighth operating step 108, the pressure effect on the differential pressure measurement is compensated by means of the common mode offset $G_{Bias}$ 230, which was determined during the calibration and is stored in the memory 40 as a first correction parameter 400, by means of the relationship $X22_{DBm} = X2_{DBm} - G_{Bias}$ 230 and converted into differential pressure measured values $X22_{DBm}$ 38 freed from the common mode offset $G_{Bias}$ 230, i) in a ninth operating step 109, the compensated differential pressure measured values $X22_{DBm}$ 38 are converted into flow values $XF_n$ 51 based on standard conditions by means of a systematic and typical pressure-vs.-flow characteristic $Z_{LFE}$ 41 of the laminar flow element 9 (FIG. 1) stored in memory 40, taking into account the second correction parameter 500 and including a current temperature measured value $T_A$ 42 and the ambient air pressure value $X13_A$ 32, j) the continuous sequence of determined flow values $XF_n$ 51 is integrated in a tenth operating step 110 into a admitted gas volume XV 52 and the admitted gas volume $XF_n$ 51 is compared with a desired volume YV 36, and k) there is a jump-back into the sixth operating step 106 in an eleventh operating step 111 in a continuous sequence until the measuring operation is ended when the desired volume YV 36 is exceeded by pump 20 (FIG. 1) being stopped by control and regulating unit 30 (FIG. 1) and by the colorimetric analysis of test gas tube 60 (FIG. 1) being performed in the control and regulating unit 30 (FIG. 1).

Figure 4B:
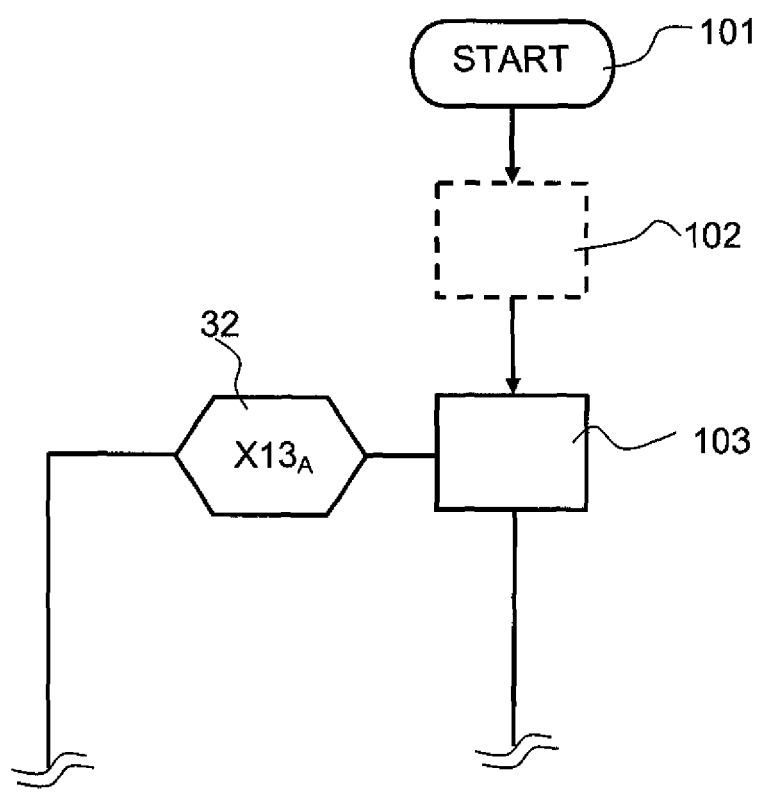
FIG. 4b is a second flow chart for operating the first or alternative gas sampling device.

FIG. 4b shows a second flow chart for operating the second gas sampling device 10 according to FIG. 2 and of the first gas sampling device 1 according to FIG. 1

The process corresponds essentially to the flow chart of the second gas sampling device 10 according to FIG. 4a.

The second flow chart for operation according to this FIG. 4b takes into account the fact that an additional, third pressure sensor 16 (FIG. 2) is available in the gas sampling device 10 (FIG. 2) for the measurement of ambient pressure. Furthermore, this second flow chart for operation is advantageous for saving time in a measurement cycle, because the ambient pressure does not change so substantially during the duration of the measurement series in a series of measurements following each other at short time intervals that it would have to be detected again, but it is to be detected only at the time of first measurement within the measurement series. The flow chart according to this FIG. 4b is explained in more detail by highlighting the differences from FIG. 4a. The first three operating steps of a sequence of eleven operating steps are shown; the operating steps four through eleven identically correspond to the flow chart for operating the gas sampling device according to the first flow chart according to 4a for operating the gas sampling device and are not shown additionally in FIG. 4b.

The process takes place such that a) with the connection element 5 (FIG. 1) open towards the measuring environment 50 (FIG. 1), pump 20 (FIG. 1) is stopped by control and regulating unit 30 (FIG. 1) at the beginning of the measuring operation in a first operating step 101, b) the second operating step with the checking for a flow-free state is omitted in the flow chart, and c) an ambient pressure measured value $X13_A$ 32 is detected by means of a third pressure sensor 16 in a third operating step 103 and sent to control and regulating unit 30 (FIG. 2).

The following operating steps four 104 through eleven 112 correspond to the flow chart for operating the gas sampling device according to the first flow chart according to FIG. 4a for operating the gas sampling device.

Figure 5A:
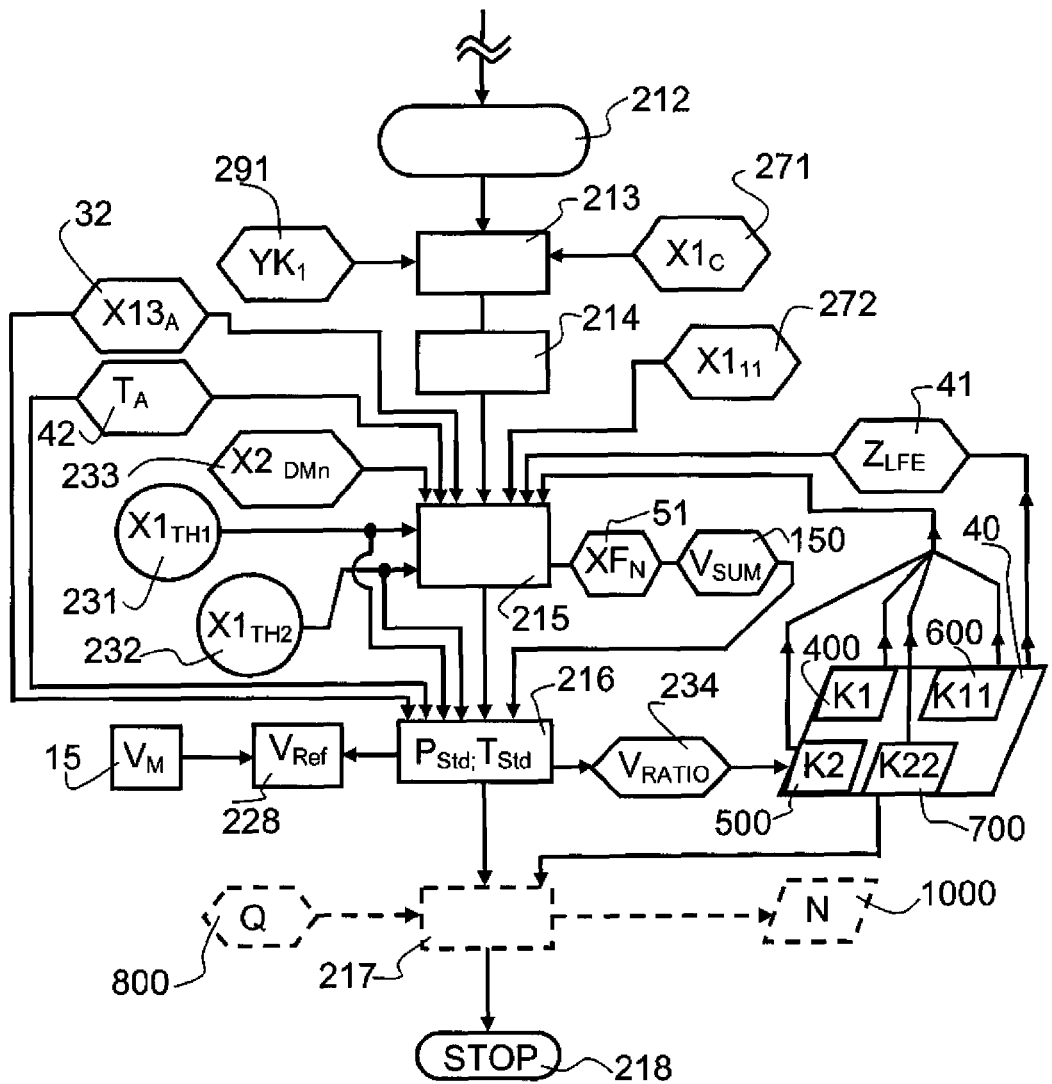
FIG. 5a is a flow chart for testing the gas sampling device at the end of the calibration.

FIG. 5a shows a flow chart for checking and expanded calibration of the gas sampling devices 1, 10 (FIGS. 1, 2) at the end 212 of a calibration according to one of the processes for calibrating the gas sampling device according to FIG. 3a or FIG. 3b subsequent to the eleventh calibration step. A sequence of five additional calibration steps and an optional additional calibration step illustrates the process according to the present invention for checking the gas sampling device in detail. The optionally additional calibration step 217 with the predetermined deviation Q 800 included in the flow chart and with a message N 1000 are indicated by broken contour lines and action lines in FIG. 5a. The process for checking and calibration takes place in a following manner:

l) a testing test gas tube is connected to connection element 5 (FIGS. 1, 2) at the end of a calibration in a twelfth calibration step 212, m) in a thirteenth calibration step 213, control and regulating unit 30 (FIG. 1) switches pump 20 (FIG. 1) on again and while continuously detecting a control pressure value $X1_c$ 271 of the first pressure sensor 12 (FIG. 1), it adjusts the pressure to the desired calibration pressure value YK1 291 in a stable manner, the closed space between connection element 5 (FIG. 1) and pump 20 (FIG. 1) is evacuated, and pump 20 (FIG. 1) is stopped when the first desired calibration pressure value $Y_{K1}$ 291 is reached, n) pump 20 (FIG. 1) is switched off at the calibration point in a fourteenth calibration step 214, o) a pressure measured value $X1_m$ 272 of the first pressure sensor 12 (FIG. 1) is detected continuously over time in a fifteenth calibration step 215 and a differential pressure signal $X2_{DMn}$ 233 of the second pressure sensor 14 (FIG. 1) is detected beginning from a when [sic—Tr.Ed.] the pressure measured value $X1_M$ 272 drops below a first pressure threshold value $X1_{TH1}$ 231 continuously over time until the pressure measured value $X1_M$ 272 drops below a second pressure threshold value $X1_{TH2}$ 232 and converted therefrom into flow values $XF_n$ 51 based on standard conditions, taking into account the systematic and typical pressure-vs.-flow characteristic $Z_{LFE}$ 41 of the laminar flow element 9 (FIG. 1), which is stored in memory 40, and the first correction parameters k1, k11 400, 600 being stored in memory 40 and the second correction parameters k2, k22 500, 700 being stored in memory 40 and including a current temperature measured value $T_A$ 42 and the ambient air pressure value $X13_A$ 32, and integrated into a current volume $V_{sum}$ 150, p) a reference volume $V_{ref}$ 228 converted to standard conditions in the form of $V_{ref} = V_M^* (X2_{TH2} 232 - X2_{TH1} 231)^* T_{Std}/(T_A^* P_{Std})$ is formed in a sixteenth calibration step 216 from a known volume $V_M$ 15 of the measuring set-up, the pressure threshold values $X1_{TH1}$ 231 and $X1_{TH2}$ 232, as well as ambient and standard conditions $X13_A$ 32, $P_{Std}$, $T_A$ and $T_{Std}$, the current volume $V_{sum}$ 150 is related to the reference volume $V_{ref}$ 228 and this volume ratio $V_{Ratio}$ 234 is stored in the memory as a current second correction parameter k2 500, q) the initial second correction parameter k22 700 is compared in an optional seventeenth calibration step 217 with the current second correction parameter k2 500 and when a predetermined deviation Q 800 of the current second correction parameter k2 from the initial second correction parameter k22 700 is exceeded, a message N 1000 is sent to the operating and output unit 28 (FIGS. 1, 2), r) and the process for checking and calibration has reached its end 218.

Figure 5B:
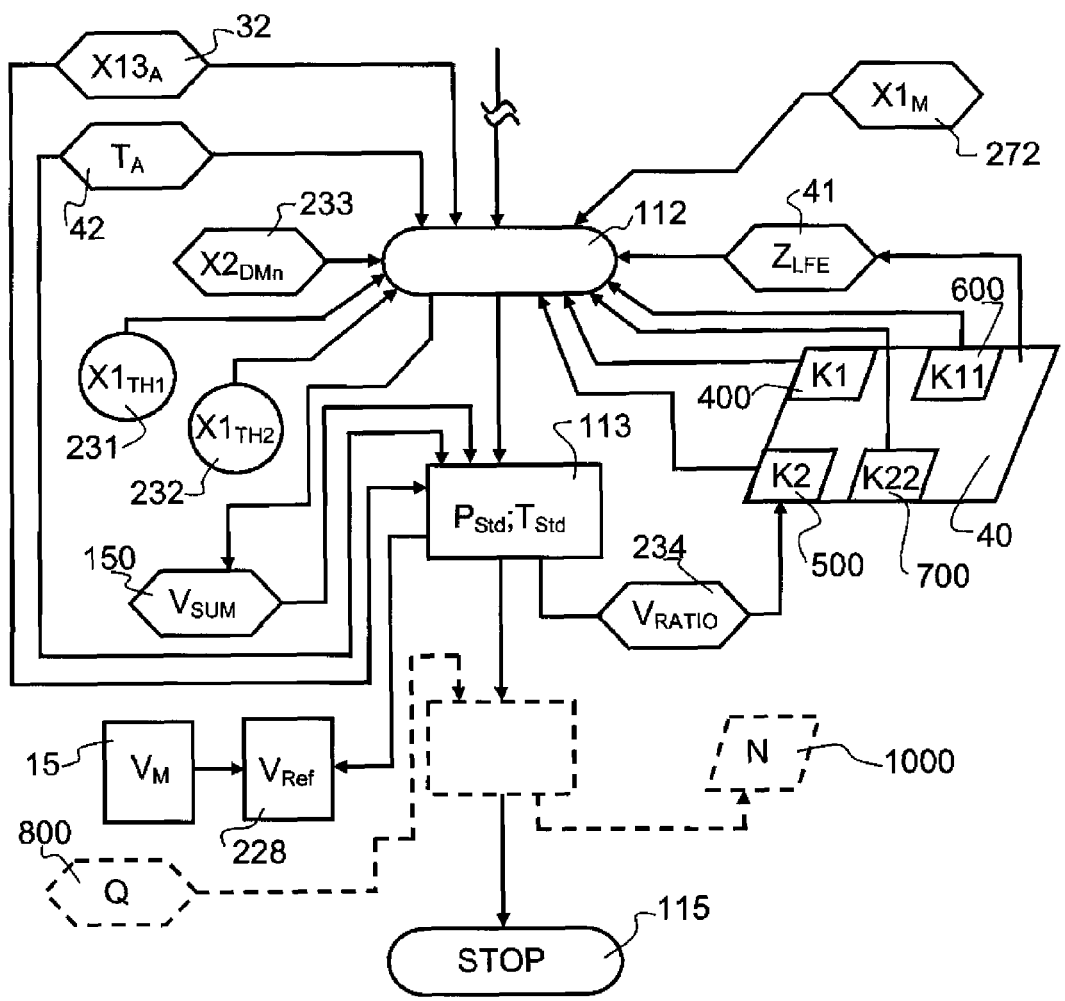
FIG. 5b is a flow chart for testing the gas sampling device at the end of the measurement.

FIG. 5b shows a flow chart for checking the gas sampling devices 1, 10 (FIGS. 1, 2) at the end 112 (FIGS. 4a, 4b) of a measurement during use according to one of the processes for operating the gas sampling device according to FIG. 4a or FIG. 4b subsequent to the eleventh operating step. A sequence of two additional operating steps with an additional optional operating step illustrates the process according to the present invention for checking the gas sampling device subsequent to the measuring operation in detail. The optionally additional operating step 114 with the predetermined deviation Q 800 included in the flow chart and with a message N 1000 are indicated by broken contour lines and action lines in FIG. 5b. The process for checking takes place in the following manner:

l) a pressure signal $X1_M$ 272 of the first pressure sensor 12 (FIG. 1) is detected continuously over time in a twelfth operating step 112 directly at the end with pump 20 (FIG. 1) shut off and a differential pressure signal $X2_{DMm}$ 233 of the second pressure sensor 14 (FIG. 1) is detected beginning when the pressure measured value $X1_M$ 272 drops below a first pressure threshold value $X1_{TH1}$ 231 continuously over time until the pressure measured value $X1_M$ 272 drops below a second pressure threshold value $X1_{TH2}$ 232, and flow values $XF_n$ 51 based on standard conditions are converted therefrom, taking into account the systematic and typical pressure-vs.-flow characteristic $Z_{LFE}$ 41 of laminar flow element 9 (FIG. 1) stored in memory 40 and the first correction parameters k1, k11 400, 600 being stored in memory 40 and the second correction parameters k2, k22 500, 700 being stored in memory 40 and including a current temperature measured value $T_A$ 42 and the ambient air pressure value $X13_A$ 32, and integrated into a current volume $V_{sum}$ 150 converted to standard conditions, m) a reference volume $V_{ref}$ 228 converted to standard conditions in the form of $V_{ref} = V_M^* (X1_{TH2} 232 - X1_{TH1} 231)^* T_{Std}/(T_A^* P_{Std})$ is formed in a thirteenth operating step from a known volume $V_M$ 15 of the measuring set-up, the pressure threshold values $X1_{TH1}$ 231 and $X1_{TH2}$ 232, as well as ambient and standard conditions $X13_A$ 32, $P_{Std}$, $T_A$ and $T_{Std}$, the current volume $V_{sum}$ 150 is related to the reference volume $V_{ref}$ 228 and the ratio is stored in the memory as a current second correction parameter k2 500, n) the initial second correction parameter k22 700 is compared in an optional fourteenth operating step 114 with the current second correction parameter k2 500 and when a predetermined deviation 800 of the current second correction parameter k2 from the initial second correction parameter k22 700 is exceeded, a message N 1000 is sent to the operating and output unit 28 (FIGS. 1, 2), o) and the process for checking has come to an end 115.

Figure 6:
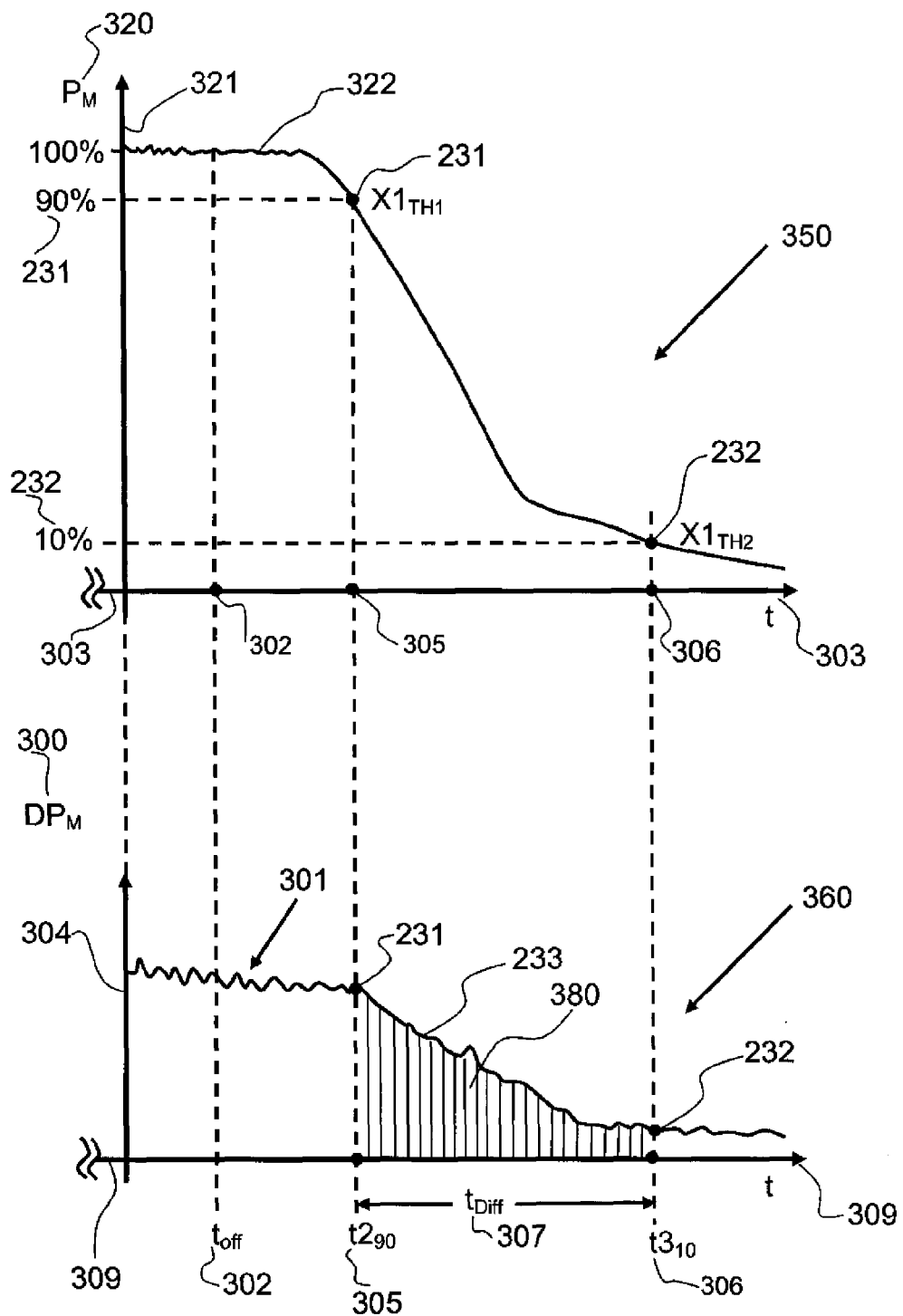
FIG. 6 is a schematic view of a pressure signal and of a differential pressure signal.

FIG. 6 shows a first schematic time curve of a signal of the first pressure sensor of the gas sampling device 1, 10 according to FIG. 1 or FIG. 2 as an upper diagram 350 with a first abscissa 303 and a first ordinate 321 and a second schematic time curve of a signal of the second pressure sensor of the gas sampling device 1, 10 according to FIG. 1 or FIG. 2 as a lower diagram 360 with a second abscissa 309 and a second ordinate 304. A pressure signal curve $P_M$ 320 of the first pressure sensor 12 (FIGS. 1, 2) and a differential pressure signal curve $DP_M$ 300 begin on the abscissas 303, 309 with the location of the ordinates 321, 304 at any point in the measurement range. The time is plotted in a dimensionless form on the abscissas 303, 309 and the pressure signal curve $P_M$ 320 is plotted on the first ordinate 321 at any desired working point of gas sampling devices 1, 10 (FIGS. 1, 2) standardized to a first signal amplitude 322 of 100%. The differential pressure signal curve $DP_M$ 300 of the second pressure sensor 14 (FIGS. 1, 2) is plotted on the second ordinate 304 with any desired, exemplary signal amplitude as a second signal amplitude 301 in a dimensionless form. Diagrams 350, 360 and abscissas 303, 309 are shown in synchronous position in time in relation to one another. A switch-off time $t_{off}$ 302, at which pump 20 (FIGS. 1, 2) is switched off in the process for checking the gas sampling device according to one of FIG. 5a or 5b, is marked on ordinates 303, 309. A first pressure threshold value $X1_{TH1}$ 231 and a second pressure threshold value $X1_{TH2}$ 232 are shown in the time course of the pressure signal curve $P_M$ 320. The first pressure threshold value $X1_{TH1}$ 231 is set at a value of 90% of the first signal amplitude 322 of the first pressure sensor 12 (FIGS. 1, 2), and the second pressure threshold value $X1_{TH2}$ 232 is set at a value of 10% of the first signal amplitude 321 of the first pressure sensor 12 (FIGS. 1, 2). The times $t2_{90}$ 305 and $t3_{10}$ 306 corresponding to the pressure threshold values $X1_{DBm}$ 231 and $X1_{TH2}$ 232 are marked on the first abscissa 303 and are transferred as reference lines into the lower diagram 360 onto the second abscissa 309. The difference between times t2 and t3 yields a time difference $t_{Diff}$ 307. The area 308 defined integrally by the positions of the points $X1_{TH1}$ 231, $X1_{TH2}$ 232 and $t2_{90}$ 305, $t3_{10}$ 306, which is shown as a shaded area in the lower diagram 360, yields graphically the current $V_{Sum}$ 150 (FIGS. 5a, 5b) flowing through the gas sampling device 1, 10 (FIGS. 1, 2) during the time difference $t_{Diff}$ 307 from the differential pressure signal curve $DP_M$ 300 with conversion on the basis of the pressure-vs. flow characteristic $Z_{LFE}$ of laminar flow element 41 (FIGS. 1, 2, 4a, 5a, 5b) and the inclusion of the current correction parameters k1, k2 in a flow value. The pressure signal curve $P_M$ 320 shown in the upper diagram 350 schematically shows a drop curve of the pressure signal $X1_M$ 272 (FIGS. 5a, 5b), which is detected and analyzed and used to determine the pressure threshold values $X1_{TH1}$ 231, $X1_{TH2}$ 232 in the process for checking the gas sampling device according to one of the FIG. 5a or 5b. The differential pressure signal curve $DP_M$ 300 shown in the lower diagram 360 schematically shows a drop curve of the differential pressure signal $X2_{DMn}$ 233 (FIGS. 5a, 5b), as it is detected, analyzed and used to determine the second correction parameters k2

500; k22 700 (FIGS. 5a, 5b) in the process for checking the gas sampling device according to one of FIG. 5a or 5b.

While specific embodiments of the invention have been shown and described in detail to illustrate the application of the principles of the invention, it will be understood that the invention may be embodied otherwise without departing from such principles.

APPENDIX

List of Reference Numbers

| | |
|---|---|
| 1 | First gas sampling device |
| 5 | Connection element |
| 6 | Energy charging and interface device |
| 7 | Filter element |
| 8 | Power pack |
| 9 | Laminar flow element (flow resistance) |
| 10 | Second gas sampling device |
| 11 | Buffer volume |
| 12 | First pressure sensor |
| 13 | Reader |
| 14 | Second pressure sensor |
| 15 | Volume of gas sampling device $V_M$ |
| 16 | Third pressure sensor |
| 17 | Energy supply unit |
| 18 | Connection lines |
| 19 | Data interface |
| 20 | Pump |
| 21 | First signal line |
| 22 | Second signal line |
| 23 | Third signal line |
| 24 | Measuring lines |
| 26 | First data connection |
| 27 | Second data connection |
| 28 | Operating and output unit |
| 29 | Inductive charging and holding element |
| 30 | Control and regulating unit |
| 31 | First differential pressure measured value $X2_{D1}$ |
| 32 | Ambient pressure measured values $X13_A$ |
| 33 | Desired vacuum value $VP_{Tube}$ |
| 34 | First desired operating pressure value $Y_B$ |
| 35 | Pressure measured value $X1_M$ |
| 36 | First desired volume YV |
| 37 | Differential pressure measured value $X2_{DMn}$ |
| 38 | Differential pressure measured values $X22_{DMn}$ freed from the common mode offset |
| 39 | Gas outlet element |
| 40 | Memory |
| 41 | Pressure-vs. flow characteristic $Z_{LFE}$ of laminar flow element |
| 42 | Ambient temperature $T_A$ |
| 43 | Third data connection |
| 44 | Fourth data connection |
| 45 | Fifth data connection |
| 46 | Sixth data connection |
| 47 | First supply line |
| 48 | Second supply line |
| 49 | Testing means |
| 50 | Measuring environment |
| 51 | Flow values $XF_n$ |
| 52 | Admitted gas volume $X_V$ |
| 55 | Sealing elements |
| 60 | Test gas tube |
| 61 | First vacuum value $VP_{K1}$ |
| 101-114 | Sequence of operating steps for measuring operation |
| 121 | First measuring connection |
| 141 | Second measuring connection |
| 142 | Third measuring connection |
| 150 | Current volume $V_{sum}$ |
| 161 | Fourth measuring connection |
| 201-217 | Sequence of calibration steps for calibration operation |
| 220 | Third calibration measured value $X1_{K1}$ |
| 221 | Fourth calibration measured value $X2_{K1}$ |
| 222 | First common mode value $X2_{Bias\_1-0}$ |
| 223 | Second desired calibration pressure value $Y_{K2}$ |
| 225 | Fifth calibration measured value $X1_{K2}$ |
| 226 | Sixth calibration measured value $X2_{K2}$ |
| 227 | Second common mode value $X2_{Bias\_2-0}$ |
| 228 | Reference volume $V_{ref}$ 228 |
| 229 | Second desired calibration pressure value $Y_{K2}$ |
| 230 | Inphase amplification $G_{Bias}$ |
| 231 | First pressure threshold value $X1_{TH1}$ |
| 232 | Second pressure threshold value $X1_{TH2}$ |
| 233 | Differential pressure measured values $X2_{DMn}$ |
| 241 | Second differential pressure measured value $X2_{D2}$ |
| 251 | First calibration measured value $X1_{K0}$ |
| 261 | Second calibration measured value $X2_{K0}$ |
| 271 | Control pressure value $X1_c$ |
| 272 | Pressure measured value $X1_m$ |
| 281 | Third differential pressure measured value $X2_{D3}$ |
| 291 | First desired calibration pressure value $Y_{K1}$ |
| 300 | Differential pressure measured values $DP_M$ |
| 301 | Second signal amplitude |
| 302 | Switch-off time $t_{off}$ |
| 303 | Abscissa |
| 304 | Second ordinate |
| 305 | Time $t2_{90}$ |
| 306 | Time $t3_{10}$ |
| 307 | Time difference $t_{Diff}$ |
| 308 | Area |
| 309 | Second abscissa |
| 320 | Pressure measured values $P_M$ |
| 321 | First ordinate |
| 322 | First signal amplitude |
| 350 | Upper diagram |
| 360 | Lower diagram |
| 400 | First correction parameter k1 |
| 500 | Second correction parameter k2 |
| 600 | Initial first correction parameter k112 |
| 700 | Initial second correction parameter k22 |
| 800 | Deviation Q |
| 1000 | Message N |

What is claimed is:

1. A process for operating a gas sampling device for colorimetric gas analysis, the process comprising the steps of:
providing a control and regulating unit, an energy supply unit, a memory, a laminar flow element, a first pressure sensor measuring absolute pressure, a second pressure sensor as a differential pressure sensor measuring a differential pressure across the laminar flow element and a pump;
performing a volume measurement and a flow measurement in one measuring operation by means of the laminar flow element and the differential pressure sensor;
measuring the absolute pressure with the first pressure sensor; and
using at least one initial correction parameter and at least one current correction parameter as the correction parameter for the conversion of the differential pressure value into a volume value, said correction factor being a function of the absolute pressure as measured by the first pressure sensor.

2. A process in accordance with claim 1, wherein the at least one initial correction parameter and/or at least one current correction parameter are stored as a first correction parameters in the memory and wherein the first correction parameters comprise an inphase amplification of a signal from the differential pressure sensor.

3. A process in accordance with claim 1, wherein the correction parameters are stored as second correction parameters in the memory, wherein the second correction parameters comprise properties of laminar flow element and/or properties of a gas.

4. A process in accordance with claim 1, wherein the first correction parameter is stored in memory as an initial first correction parameter within the framework of a final testing of the gas sampling device.

5. A process in accordance with claim 1, wherein the second correction parameter is stored in memory as an initial second correction parameter within the framework of a final testing of the gas sampling device.

6. A process in accordance with claim 1, wherein the initial second correction parameter is compared with a current second correction parameter and a message is sent to an operating and output unit in case of a deviation.

7. A process in accordance with claim 2, wherein measured values of the first pressure sensor and measured values of the differential pressure sensor are detected at at least two calibration points to determine the inphase amplification with the air supply shut off at a connection element, wherein the at least two calibration points have different pressure levels, and an inphase amplification of the signal from the differential pressure sensor is determined from the measured values of the first pressure sensor and of the differential pressure sensor and is stored as a first correction parameter in the memory.

8. A process in accordance with claim 3, wherein the properties of laminar flow element, which are contained in the second correction parameters and are stored in the memory comprise a flow resistance of laminar flow element.

9. A process in accordance with claim 3, wherein the properties of the gas, which are contained in the second correction parameters and are stored in the memory, comprise the viscosity of the gas.

10. A process in accordance with claim 3, wherein:
after switching off the pump, the measured values of the differential pressure sensor are detected continuously over time from a first pressure threshold value to a second pressure threshold value;
a current volume is determined integrally, taking into account the pressure-vs. flow characteristic of the laminar flow element;
a reference volume is calculated from the current ambient and standard conditions for pressure and temperature;
the calculated reference volume is put into a volume ratio with the integrally determined current volume; and
the volume ratio is stored in memory as a second correction parameter.

11. A process for operating a gas sampling device for colorimetric gas analysis, the process comprising the steps of:
providing a control and regulating unit, an energy supply unit, a memory, connection lines, a laminar flow element, a first pressure sensor measuring absolute pressure, a second pressure sensor as a differential pressure sensor measuring a differential pressure across the laminar flow element and a pump;
operatively connecting the connection lines, the laminar flow element, the pressure sensor, the differential pressure sensor and the pump;
performing a volume measurement and a flow measurement in one measuring operation by measuring a pressure change across the laminar flow element with the differential pressure sensor to from a differential pressure value;
measuring the absolute pressure in one of the connection lines with the first pressure sensor;
forming at least one initial correction parameter and at least one current correction parameter as a correction parameter as a function of the absolute pressure as measured by the first pressure sensor; and
converting the differential pressure value into a volume value using the correction parameter.

12. A process in accordance with claim 11, wherein the correction parameter is stored as a first correction parameter in the memory and wherein the first correction parameter comprises an inphase amplification of a signal from the differential pressure sensor.

13. A process in accordance with claim 11, wherein the first correction parameter is stored in memory as an initial first correction parameter within the framework of a final testing of the gas sampling device.

14. A process in accordance with claim 12, further comprising providing a connection element connected to the connection lines wherein:
measured values, at least two calibration points, of the first pressure sensor and measured values of the differential pressure sensor are detected to determine the inphase amplification with a connection to the environment or to an air supply shut off at the connection element;
the at least two calibration points have different pressure levels, and an inphase amplification of the signal from the differential pressure sensor is determined from the measured values of the first pressure sensor and of the differential pressure sensor and is stored as the first correction parameter in the memory.

15. A process in accordance with claim 12, wherein correction parameters are stored as second correction parameters in the memory, wherein the second correction parameters comprise properties of laminar flow element and/or properties of a gas.

16. A process in accordance with claim 15, wherein the properties of the laminar flow element, which are contained in the second correction parameters and are stored in the memory comprise a flow resistance of the laminar flow element.

17. A process in accordance with claim 15, wherein the properties of the gas, which are contained in the second correction parameters and are stored in the memory, comprise the viscosity of the gas.

18. A process in accordance with claim 15, wherein:
after switching off the pump, measured values of the differential pressure sensor are detected continuously over time from a first pressure threshold value to a second pressure threshold value;
a current volume is determined integrally, taking into account the pressure-vs. flow characteristic of the laminar flow element;
a reference volume is calculated from the current ambient and standard conditions for pressure and temperature;
the calculated reference volume is put into a volume ratio with the integrally determined current volume; and
the volume ratio is stored in memory as a second correction parameter.

19. A process for operating a gas sampling device, the process comprising the steps of:
providing a connection element adapted to receive a gas sample;
providing a laminar flow element with a flow connection to the connection element;
providing a first pressure sensor measuring an absolute pressure in the flow connection between the connection element and the laminar flow element;
providing a pump with a flow connection to the laminar flow element;
providing a second pressure sensor as a differential pressure sensor measuring a pressure change across the laminar flow element;
measuring the absolute pressure with the first pressure sensor;
operating the pump to flow the gas sample from the connection element through the laminar flow element;

measuring the differential pressure across the laminar flow element with the differential pressure sensor while the pump is flowing the gas sample through the laminar flow element;
determining a correction factor from the absolute pressure measured with the first pressure sensor;
converting the measured differential pressure into a volume value using the correction parameter.

20. A process in accordance with claim 19, wherein:
the connection element is adapted to receive a test gas tube for colorimetric gas analysis.

* * * * *